US011123712B2

(12) United States Patent
Lail et al.

(10) Patent No.: US 11,123,712 B2
(45) Date of Patent: Sep. 21, 2021

(54) CATALYSTS UTILIZING CARBON DIOXIDE FOR THE EPOXIDATION OF OLEFINS

(71) Applicant: Research Triangle Institute, Research Triangle Park, NC (US)

(72) Inventors: Marty Lail, Raleigh, NC (US); Paul Mobley, Raleigh, NC (US); Jonathan Peters, Durham, NC (US); Sree Nandita Akunuri, Raleigh, NC (US); Joshua J. Hlebak, Raleigh, NC (US)

(73) Assignee: RESEARCH TRIANGLE INSTITUTE, Research Triangle Park (NC)

( * ) Notice: Subject to any disclaimer, the term of this patent is extended or adjusted under 35 U.S.C. 154(b) by 96 days.

(21) Appl. No.: 16/320,116

(22) PCT Filed: Jul. 26, 2017

(86) PCT No.: PCT/US2017/043921
§ 371 (c)(1),
(2) Date: Jan. 24, 2019

(87) PCT Pub. No.: WO2018/022740
PCT Pub. Date: Feb. 1, 2018

(65) Prior Publication Data
US 2019/0270073 A1 Sep. 5, 2019

Related U.S. Application Data

(60) Provisional application No. 62/366,795, filed on Jul. 26, 2016.

(51) Int. Cl.
*C01B 32/40* (2017.01)
*B01J 23/68* (2006.01)
(Continued)

(52) U.S. Cl.
CPC .......... *B01J 23/686* (2013.01); *B01J 21/04* (2013.01); *B01J 23/6525* (2013.01);
(Continued)

(58) Field of Classification Search
CPC ..... C07D 301/03; B01J 37/088; B01J 37/035; B01J 37/0236; B01J 23/6525;
(Continued)

(56) References Cited

U.S. PATENT DOCUMENTS 2,781,295 A * 2/1957 Teter ................... C10G 45/04
208/216 R
2,799,661 A * 7/1957 De Rosset ............ B01J 23/28
502/314

(Continued)

FOREIGN PATENT DOCUMENTS

CN 104370692 A 2/2015
EP 0266015 B1 12/1991
(Continued)

OTHER PUBLICATIONS

Shen, J., et al. "Mechanistic study of CO formation from CO2 using a mixed-metal oxide of tin, iron, and aluminum†." RSC Adv., 2014, 45198-45206, 4 (85), Royal Society of Chemistry, London.
(Continued)

*Primary Examiner* — Taylor V Oh
(74) *Attorney, Agent, or Firm* — Nathan P. Letts; Olive Law Group, PLLC

(57) ABSTRACT

The present disclosure provides mixed molybdenum oxide catalysts, methods for preparing epoxides from olefins and CO2 using them, and methods of making the mixed molybdenum oxide catalysts by impregnation or co-precipitation. In a preferred embodiment, the mixed molybdenum oxide catalysts are silver/molybdenum oxide catalysts, ruthenium/molybdenum oxide catalysts, or a combination thereof.

21 Claims, 17 Drawing Sheets

(51) Int. Cl.

| | | |
|---|---|---|
| *B01J 21/04* | (2006.01) | |
| *B01J 23/652* | (2006.01) | |
| *B01J 37/02* | (2006.01) | |
| *B01J 37/03* | (2006.01) | |
| *B01J 37/08* | (2006.01) | |
| *C07D 301/03* | (2006.01) | |
| *B01J 29/03* | (2006.01) | |

(52) U.S. Cl.
CPC ....... *B01J 29/0325* (2013.01); *B01J 37/0236* (2013.01); *B01J 37/033* (2013.01); *B01J 37/035* (2013.01); *B01J 37/088* (2013.01); *C01B 32/40* (2017.08); *C07D 301/03* (2013.01)

(58) Field of Classification Search
CPC ........ B01J 23/686; B01J 21/04; B01J 37/033; B01J 29/0325; C01B 32/40
USPC .............................................. 423/230, 418.2
See application file for complete search history.

(56) References Cited

U.S. PATENT DOCUMENTS

| | | |
|---|---|---|
| 5,686,380 A | 11/1997 | Pitchai et al. |
| 6,750,173 B2 | 6/2004 | Rizkalla et al. |
| 2014/0288335 A1 | 9/2014 | Yoshii et al. |
| 2015/0183701 A1 | 7/2015 | Blank et al. |

FOREIGN PATENT DOCUMENTS

| | | |
|---|---|---|
| WO | 2004058633 A2 | 7/2004 |
| WO | WO 2015/020862 A2 * | 2/2015 |

OTHER PUBLICATIONS

"Ethylene Oxide." Kirk-Othmer Enxyclopedia of Chemical Technology. vol. 10. pp. 632-673.
Chongterdtoonskul, Atiporn et al. 2012. "Effects of oxide supports on ethylene epoxidation activity over Ag-based catalysts." Journal of Molecular Catalysis A: Chemical. vol. 358, pp. 58-66.
Colmenares, Juan Carlos. 2010. Novel Trends in the Utilization of CO2 as a Reagent and Mild Oxidant in the C—C Coupling Reactions. Current Organic Synthesis. vol. 7. Pages 533-542.
Dellamorte, J.C. et al. 2007. "Rhenium promotion of Ag and Cu—Ag bimetallic catalysts for ethylene expoxidation." Catalysis Today vol. 120. pp. 182-185.
Epoxide. Wikipedia. Accessed Jul. 18, 2016 (five (5) pages).
Ethylene oxide. Wikipedia. Accessed Jul. 12, 2016. (nineteen (19) pages).
Guojie, Jin et al. "Effect of additive in feedstock on performance of AG—Mo03/Zr02 catalyst for propylene epoxidation by molecular oxygen." Reaction Kinetics and Catalysis Letters, vol. 89, No. 2, pp. 253-260.
International Search Report and Written Opinion issued in counterpart PCT Application No. PCT/US2017/043921 dated Sep. 6, 2018.
Kolb, Kenneth E, and Kolb, Doris. 1983. "Organic Chemicals from Carbon Monoxide." Real World of Industrial Chemistry. vol. 60. No. 1. pp. 57-59.
Lambert, Richard M., et al. "Heterogeneous alkene epoxidation: past, present and future." 2005. Journal of Molecular Catalysis A: Chemical. vol. 228. pp. 27-33.
Propylene oxide. Wikipedia. Accessed Jul. 18, 2016 (three (3) pages).
Tsuji, Junpei. 2006. "Development of New Propylene Oxide Process." Sumitomo Kagaku. vol. 2006-I. pp. 1-8.
International Preliminary Report on Patentability issued in counterpart PCT Application No. PCT/US2017/043921 dated Jan. 29, 2019 (twelve (12) pages).

* cited by examiner

CATALYSTS UTILIZING CARBON DIOXIDE FOR THE EPOXIDATION OF OLEFINS

CROSS REFERENCE TO RELATED APPLICATIONS

This application is a § 371U.S. National Stage of International Application PCT/US2017/043921, filed 26 Jul. 2017 having, which claims the benefit of 62/366,795 filed Jul. 26, 2016, Lail et al., which are hereby incorporated by reference in their entireties.

1. FIELD

The present disclosure provides novel mixed molybdenum catalysts, methods for preparing epoxides from olefins, and methods of making the mixed molybdenum catalysts. In one embodiment, the mixed molybdenum catalysts may be silver/molybdenum catalysts, ruthenium/molybdenum catalysts, or a combination thereof.

2. BACKGROUND

2.1. Introduction: Preparation of Epoxides

Most ethylene oxide (EtO) is produced commercially by silver catalyzed oxidation of ethylene using either air or high purity oxygen (>95 mol %). Dever et al "Ethylene Oxide" in Kirk-Othmer Encyclopedia of Chemical Technology Mar. 14, 2004. Propylene oxide is prepared either by a hydrochlorination of propylene, air oxidation with cumene with a titanium catalyst, or oxidation using hydrogen peroxide producing styrene or t-butanol as a co-product. Tsuji et al. 2006R&D Report, "SUMITOMO KAGAKU", vol. 2006-I (www.sumitomo-chem.co.jp/english/rd/report/theses/docs/20060100_ely.pdf accessed 2016 Jul. 19).

Chongterdtoonskul et al. disclose a variety of silver based catalysts including a 17.16 wt % Ag/SrTiO$_3$ for selective ethylene epoxidation with oxygen. See Chongterdtoonskul, et al., Comparative study on the influence of second metals on Ag-loaded mesoporous SrTiO$_3$ catalysts for ethylene oxide evolution. *Journal of Molecular Catalysis A: Chemical* 2013, 372, 175-182.

Dellamorte et al. disclose rhenium promoted Ag and Cu—Ag bimetallic catalysts for preparing ethylene oxide from ethylene and oxygen feed. See Dellamorte et al., Rhenium promotion of Ag and Cu—Ag bimetallic catalysts for ethylene epoxidation. *Catal. Today* 2007, 120, 182-185.

Lambert et al. disclose single crystal studies of silver and copper to study the i-adsorbed alkene and adsorbed oxygen atoms (adatoms, O$_a$). They report that copper is more selective than silver when the alkene has allylic hydrogens, e.g., propylene. See Lambert et al. *Journal of Molecular Catalysis A: Chemical* 2005, 228, 27-33.

Lauritzen (EP Pat. No. 0 266 015B1) disclose a silver alumina catalyst with a surface area of less than 20 m$^2$/g and a promoting amount of rhenium. They also disclose a variety of metal promoters including molybdenum present at 10-3000 ppm by weight.

Rizkalla et al. (U.S. Pat. No. 6,750,273) disclose a silver alumina ethylene oxide catalyst where surface sodium ions have been replaced by 1-10 ppm lithium ions. They test their catalyst with a gas mixture of ethylene, oxygen and an inert gas at 300 psig.

2.2. Introduction: CO$_2$ as a Reagent

WO2015/020862 (Shen et al.) discloses iron (II/III) catalysts for the extraction of oxygen from CO$_2$ and reactions with organic compounds including a schematic showing formation of epoxides from alkenes. Others have reported studies of CO$_2$ as a reagent for organic synthesis. See Colmenares, Novel Trends in the Utilization of CO$_2$ as a Reagent and Mild Oxidant in the C—C Coupling Reactions, Current Organic Synthesis 2010, 7(6), 533-542.

3. SUMMARY OF THE DISCLOSURE

The present disclosure provides a mixed molybdenum oxide catalyst which comprises a silver oxide, a ruthenium oxide, or a mixture thereof, for catalyzing the carbon dioxide oxidation of an organic compound containing one or more carbon-carbon double bonds to an organic epoxide compound.

The mixed molybdenum oxide catalyst above may further comprise a Group IA or Group IIA element promoter.

The mixed molybdenum oxide catalyst above may further comprise a support.

The mixed molybdenum oxide catalyst of above the support may be Al$_2$O$_3$, SiO$_2$, TiO$_2$, ZrO$_2$, AlPO$_4$, activated carbon, graphite, or a mixture thereof.

In an embodiment, the mixed molybdenum oxide catalyst above may be a mixed silver/molybdenum oxide catalyst. The molar ratio of Ag$_2$O to MoO$_3$ may be in the range of about 1.0 to 0.05 to about 1.0 to 20.0, about 1.0 to 0.1 to about 1.0 to 10.0, about 1.0 to 0.5 to about 1.0 to 5.0, or about 1.0 to 1.0 to about 1.0 to 4.0.

In another embodiment, the mixed molybdenum oxide catalyst above may be a mixed ruthenium/molybdenum oxide catalyst. The molar ratio of RuO$_2$ to MoO$_3$ is in the range of about 1.0 to 0.05 to about 1.0 to 20.0, about 1.0 to 0.1 to about 1.0 to 10.0, about 1.0 to 0.5 to about 1.0 to 5.0, or about 1.0 to 1.0 to about 1.0 to 4.0.

In yet another embodiment, the mixed molybdenum oxide catalyst above may be a mixed silver/ruthenium/molybdenum oxide catalyst. In the mixed silver/ruthenium/molybdenum oxide catalyst the molar ratio of Ag$_2$O to MoO$_3$ is in the range of about 1.0 to 0.05 to about 1.0 to 20.0 and the molar ratio of RuO$_2$ to MoO$_3$ is in the range of about 1.0 to 0.05 to about 1.0 to 20.0. Alternatively, the molar ratio of Ag$_2$O to MoO$_3$ may be in the range of about 1.0 to 0.1 to about 1.0 to 10.0, about 1.0 to 0.5 to about 1.0 to 5.0, or about 1.0 to 1.0 to about 1.0 to 4.0 and the molar ratio of RuO$_2$ to MoO$_3$ is in the range of about 1.0 to 0.1 to about 1.0 to 10.0, about 1.0 to 0.5 to about 1.0 to 5.0, or about 1.0 to 1.0 to about 1.0 to 4.0.

The organic compound containing one or more carbon-carbon double bonds may be an alkene and the organic epoxide compound may be an alkene oxide, e.g., alkene is ethylene and the alkene oxide is ethylene oxide.

The disclosure also provides a method for converting an olefin to an epoxide which comprises contacting the olefin with a mixed molybdenum oxide catalyst with an appropriate CO$_2$ feed stream under suitable temperature and pressure conditions so as to convert the olefin to the epoxide.

Suitable temperatures for the conversion of olefin to epoxide when combined with a CO$_2$ stream can be as low as 150° C. and as high as 550°. Preferably the temperature is between about 250° C. and about 400° C., more preferably the temperature is between about 275° C. and about 375° C., still more preferably the temperature is between about 300° C. and about 350° C.

Suitable pressures for the conversion of olefin and carbon dioxide into epoxides can be up to 30 bar or lower. The partial pressures of olefin and carbon dioxide in the feed streams can be any combination which sums to 30 bar pressure or lower. Preferably, the pressure for the conversion is between about 10 bar and about 30 bar, more preferably the pressure is between about 15 bar and about 25 bar, still more preferably the pressure is between about 22.5 bar and about 27.5 bar.

In one embodiment of the method above, the olefin, the mixed molybdenum oxide catalyst, and the appropriate $CO_2$ feed stream are reacted together at the same time. That is, all three reagents are present in the same reactor simultaneously.

In an alternative embodiment of the method above, the olefin, the mixed molybdenum oxide catalyst, and the appropriate $CO_2$ feed stream are reacted sequentially. For example, they may be reacted sequentially in a chemical looping process. The configuration for this process may be a swing operation in which $CO_2$ and the olefin are fed alternately to the reactor. In another embodiment, which may involve one or more transport reactors, the catalyst is reacted with $CO_2$ in one reactor and is moved to another reactor to where the catalyst reacts with the olefin, then the catalyst is returned to the $CO_2$ reactor.

In any of the methods above the olefin, the mixed molybdenum oxide catalyst, and the appropriate $CO_2$ feed stream are reacted together in a fluidized bed.

In any of the methods above, the olefin may be an alkene, a cycloalkene, a diene or a phenylalkene such as butadiene, butylene, ethylene, or propylene.

The disclosure also provides a method for preparing a mixed molybdenum oxide catalyst which comprises: (a) contacting a support material with a mixed metal molybdenum salt solution; (b) drying the support material and the molybdenum salt solution; and (c) calcining the dried support material and the molybdenum salt so as to prepare the mixed molybdenum oxide catalyst. The mixed metal molybdenum salt solution may be a solution of molybdenum and silver salts; a solution of molybdenum and ruthenium salts; or a combination thereof. The support material may be $Al_2O_3$.

The disclosure also provides a method for preparing a mixed molybdenum oxide catalyst which comprises: (a) contacting a solution containing mixed metal molybdenum salts and an aluminum salt with an aqueous base solution so as to form a co-precipitate; (b) drying the co-precipitate; and (c) calcining the dried co-precipitate so as to prepare the mixed molybdenum oxide catalyst. The mixed metal molybdenum salt solution may be a solution of molybdenum and silver salts; a solution of molybdenum and ruthenium salts; or a combination thereof.

4. BRIEF DESCRIPTION OF THE FIGURES

FIG. 1. Comparison of selectivity and conversion of conventional ethylene oxide catalysts (circles) to novel $CO_2$-utilizing epoxidation catalysts (triangles). RTI Cat 1 is $RuCl_3MoO_3(\gamma-Al_2O_3)_{22}$ and RTI Cat 2 is $RuCl_3MoO_3(\alpha-Al_2O_3)_{22}$.

FIG. 2. Comparison of yield and conversion of conventional oxygen-utilizing epoxidation catalysts (circles) with unconventional $CO_2$-utilizing epoxidation catalysts. In this figure the RTI catalyst is $RuCl_3MoO_3(\gamma-Al_2O_3)_{22}$.

FIG. 3. XRD results of a $RuCl_3(MoO_3)_3(Al_2O_3)_{22}$ catalyst.

FIG. 4: the reactivity of the catalyst towards ethylene and $CO_2$ when the catalyst is exposed to the feed mixture.

Figure 10:
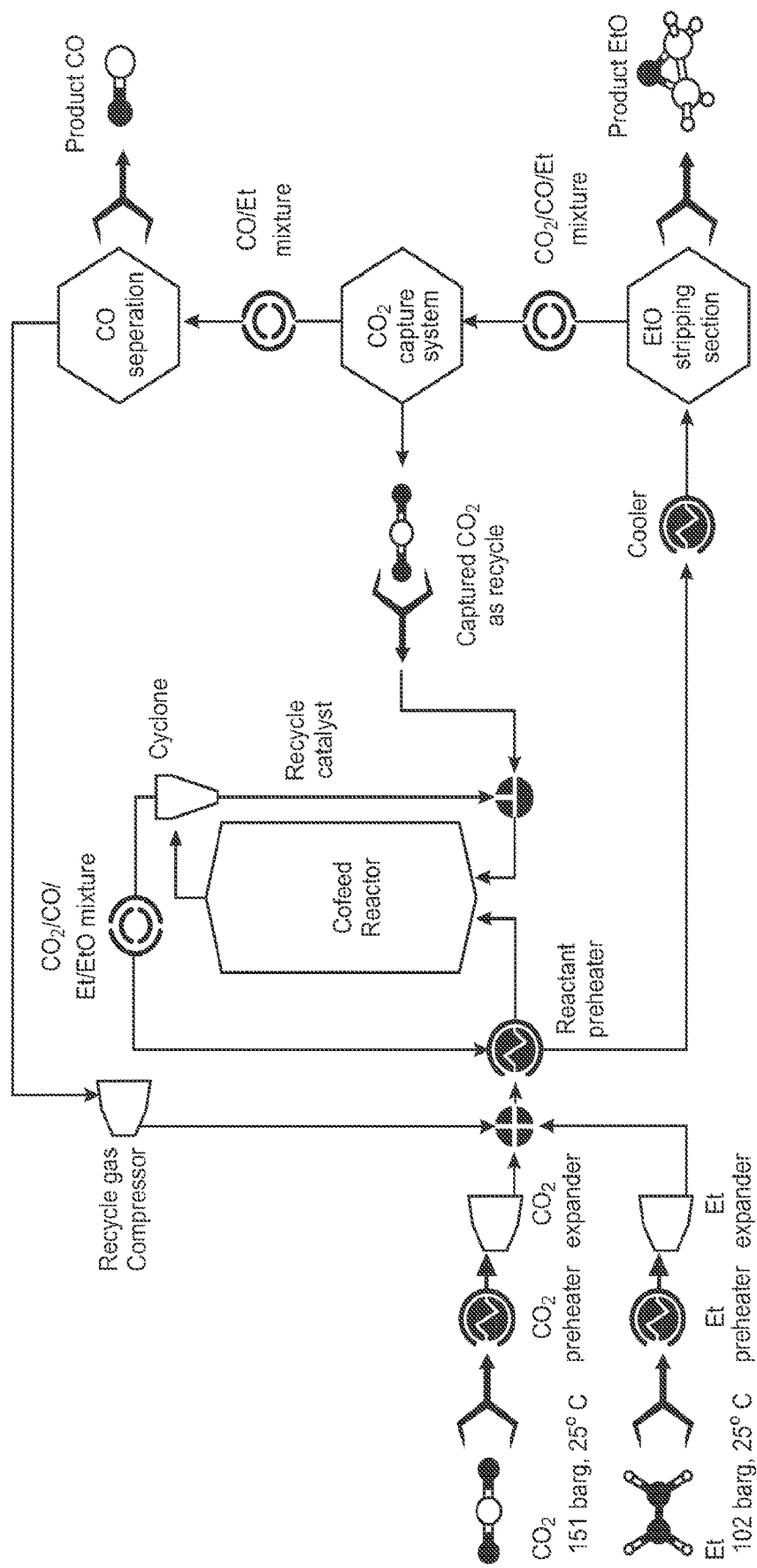

FIG. 10. Process flow diagram for $CO_2$ utilization approach for Et oxidation.

Figure 11:
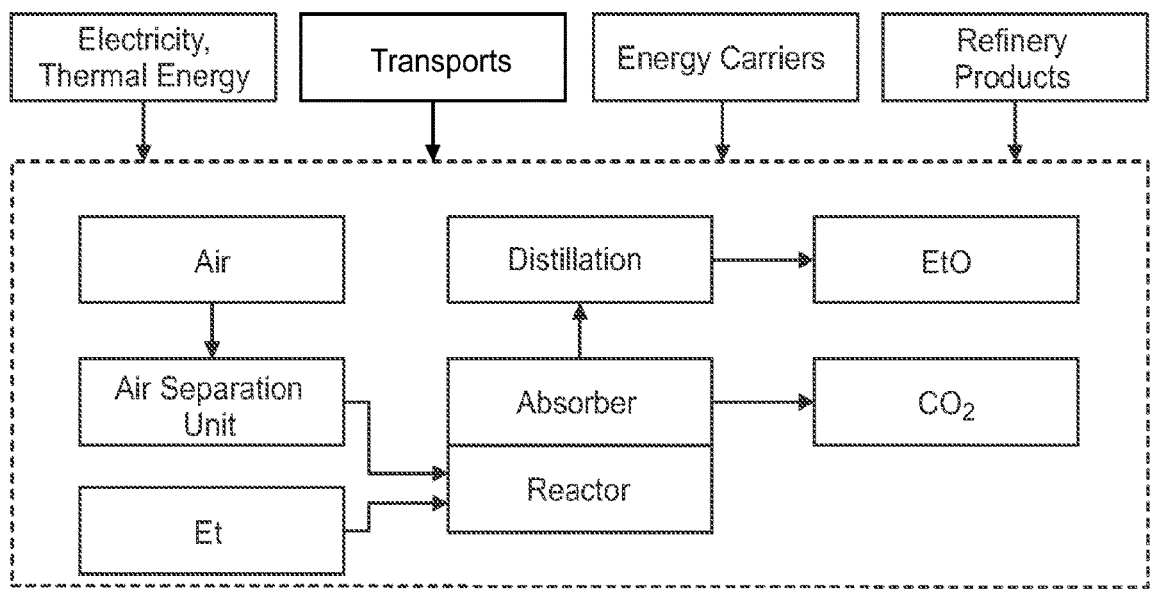

FIG. 11. A block diagram of the conventional Et oxidation process from a green house gas (GHG) perspective.

Figure 12:
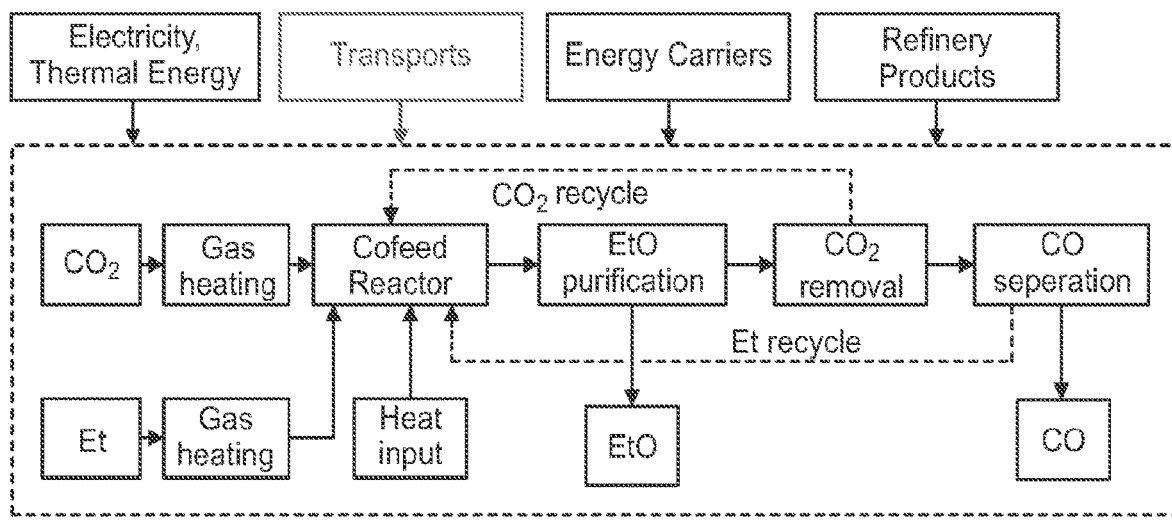

FIG. 12. A block flow diagram of the process disclosed herein from a GHG perspective.

5. DETAILED DESCRIPTION OF THE DISCLOSURE

The conventional catalysts for epoxide product do not consume $CO_2$ in the production of alkene oxides, but rather produce $CO_2$ as an undesirable emission from the process. The use of $CO_2$ has an inherent advantage in that it obviates the need for an air separation unit for obtaining purified oxygen, however it does carry the need for a purified $CO_2$ stream as feedstock. Purified $CO_2$ streams are of interest to industries which produce $CO_2$ byproducts as regulations are debated for limitation of carbon emissions in future industry activities to mitigate the risk of global warming. In addition, the invention produces two valuable product streams, alkene oxides and carbon monoxide, while the existing conventional processes only produce alkene oxides. Carbon monoxide is a widely—utilized feedstock for the production of many petrochemicals with substantial markets.

The catalysts described herein have been shown to be able to produce EtO in both a co-feed mode and a transport mode of operation. However, after incorporating experimental data into a process model, it was determined that the co-feed mode of operation is the most economical embodiment for a complete process. While the catalyst is not optimized, the current experimental results have achieved yields comparable to the conventional process with a yield of EtO between 5% and 8%. Analysis indicates that the technology could be economically viable given favorable market conditions. Optimization of the catalyst during continued development could increase the economic advantage of the technology beyond the conventional process. Modeling of the system has been performed to analyze the potential greenhouse gas (GHG) reductions of the process. Our studies show that greater than 4.7 Mt of $CO_2$ emissions may be avoided for each 1 Mt of EtO produced. Thus, one standard-sized 250 kt EtO plant would be able to achieve greater than 1 Mt of $CO_2$ emissions avoidance per annum.

A support for the mixed molybdenum catalysts is exemplified by $Al_2O_3$. One of ordinary skill in the art would recognize additional supports. Supports may be $Al_2O_3$—$SiO_2$, $CaAl_2O_4$, $CaOZrO_2$, $K_2Al_2O_4$, $MgAl_2O_4$, $MgOZrO_2$, $Na_2Al_2O_4$, $SiO_2$, $TiO_2$, $Y_2O_3ZrO_2$, $AlPO_4$, graphite, carbon, or $ZrO_2$. Other, non-catalyst heat transfer media also can be used, such as alumina, silica, olivine, and sands.

Furthermore, the catalysts may also include a promoter which will act to improve yield and/or specificity. The promoter components may be a compound having the formula $A_2O$; $A_2CO_3$; or $A(OH)$ (where A=Li, Na, K, Rb, Cs); BO; $BCO_3$; $B(OH)_2$ (where B=Mg, Ca, Sr); or a mixture of A and B compounds.

5.1. Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The reagents disclosed herein may be epoxides used to produce commercially important products including, but not limited to, 1,2-epoxy butane, 3,4-epoxy-1-butene, crown ethers, dioxane, ethanolamines, ethylene glycol, ethoxylates, polyester, polyethers, polyethylene terephthalate, polyglycols, polyols, propanoic acid, propylene glycol, and polyurethanes.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES $CO_2$-Utilizing Catalysts Compared to the Conventional Process

The invention is a novel method for making ethylene oxide and other alkene oxides by utilizing carbon dioxide and a catalyst. The invention differs from existing practices in using carbon dioxide as the source of oxygen for the alkene-oxide. The conventional process for making EtO is performed at moderate temperatures (approximately 275° C., 550° K). Through epoxidation of ethylene by using air or $O_2$ separated from air by cryogenic separators. Catalyst compositions are primarily silver supported on α-alumina with common promoters of alkali and chloride salts. Typical single-pass ethylene conversion is approximately 13%, with a 42% selectivity to EtO, and the remainder to the competing side reaction of combustion of either the ethylene feed or produced EtO. Table 1 presents data reported in the open literature for epoxidation catalysts used in an $O_2$-based process compared to the $CO_2$-based process disclosed herein. Chongterdtoonskul et al. 2013; Dellamorte et al. 2007.

TABLE 1

Comparison of Data from the Literature Regarding Epoxidation Catalysts Used in $O_2$-Based versus $CO_2$-Based Processes $$1/2\ O_2 + H_2C{=}CH_2 \xrightarrow{Ag^+\text{-catalyst}} \overset{O}{\triangle}$$

| Catalyst | Reaction Temperature (° C.) | Ethylene Conversion (%) | EtO Selectivity (%) | EtO Yield (%) |
|---|---|---|---|---|
| Ag-α-$Al_2O_3$ | 275 | 3.6 | 77.4 | 2.8 |
| Ag—$SiO_2$ | 275 | 4.4 | 86.4 | 3.8 |
| Ag—$TiO_2$ | 275 | 2.5 | 69.7 | 1.8 |
| Re—Ag—$Al_2O_3$ | 265 | 13.5 | 42.0 | 5.67 |
| RTI—$Al_2O_3$ $CO_2$* | 350 | 25.0 | 34.0 | 8.5 |

Figure 1:
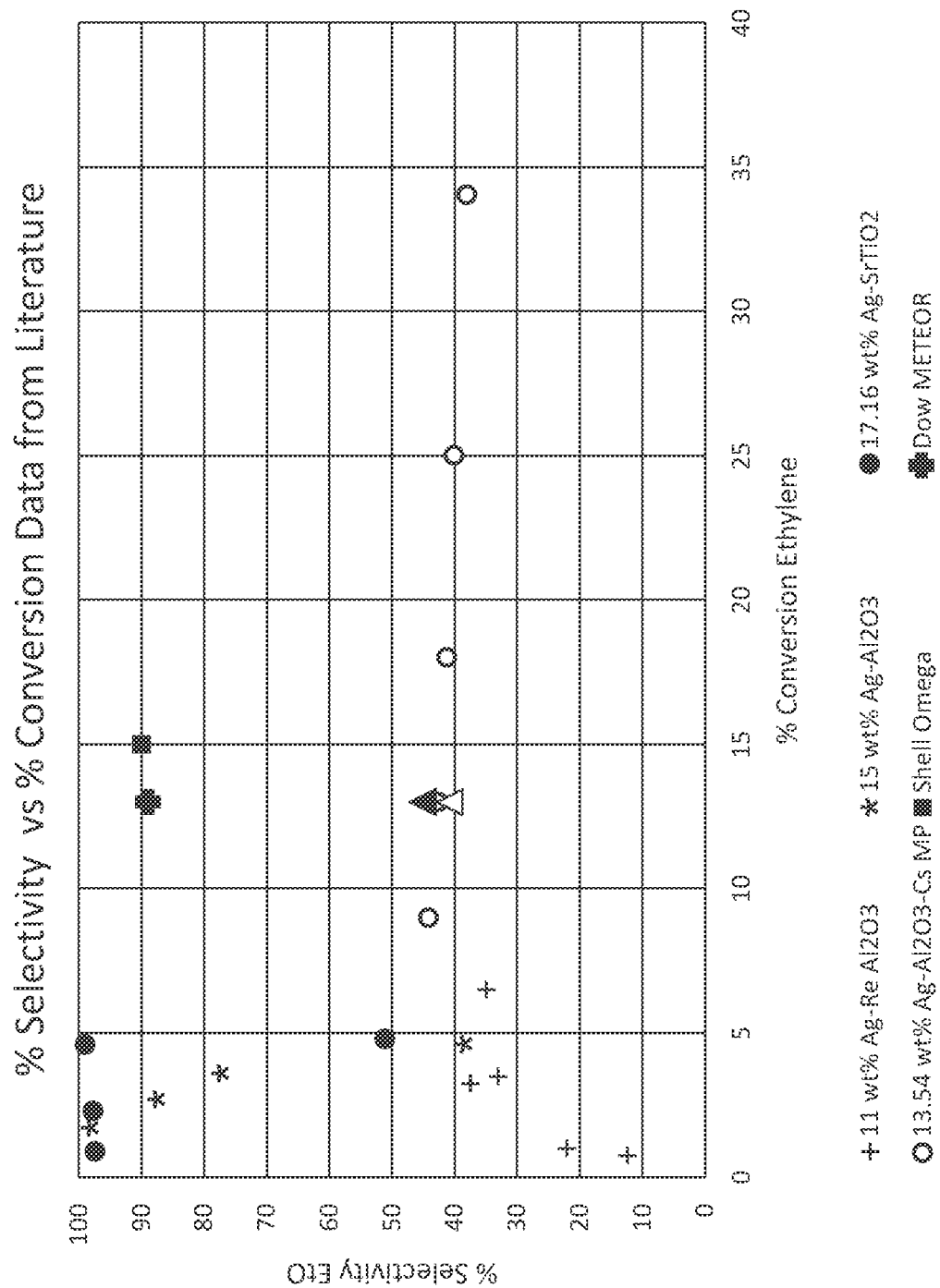

Note:
$Al_2O_3$ = alumina;
$SiO_2$ = silica;
$TiO_2$ = titania;
*$RuO_2(MoO_3)_3(Al_2O_3)_{22}$ There is limited specific information shared about industrial catalysts, however a few sources indicate that Shell produces EtO with a Ag-based catalyst operating at 10-15% conversion with 90% selectivity. Dow is reported to use a proprietary Ag-based catalyst which gives 8-13% ethylene conversion with 89% selectivity. CRI Catalyst company is part of the global catalyst technology company of the Shell Group and has developed EtO catalysts for oxygen based processes for more than 40 years. They report four families of catalysts with selectivities as high as ~88% which are used to produce more than 50% of the world's EtO, but the associated ethylene conversion numbers are not publicized, and presumably these are Ag-based catalysts similar to those reported in the open literature showing the highest selectivities. FIG. 1 summarizes the reported conversion and yield data for the catalysts detailed in the open peer-reviewed literature and described in industry reports. The data shows that the $CO_2$-utilization catalysts perform reasonably well compared to oxygen-utilizing catalysts despite $CO_2$ being an unconventional source of oxygen for a thermochemical partial oxidation.

Figure 2:
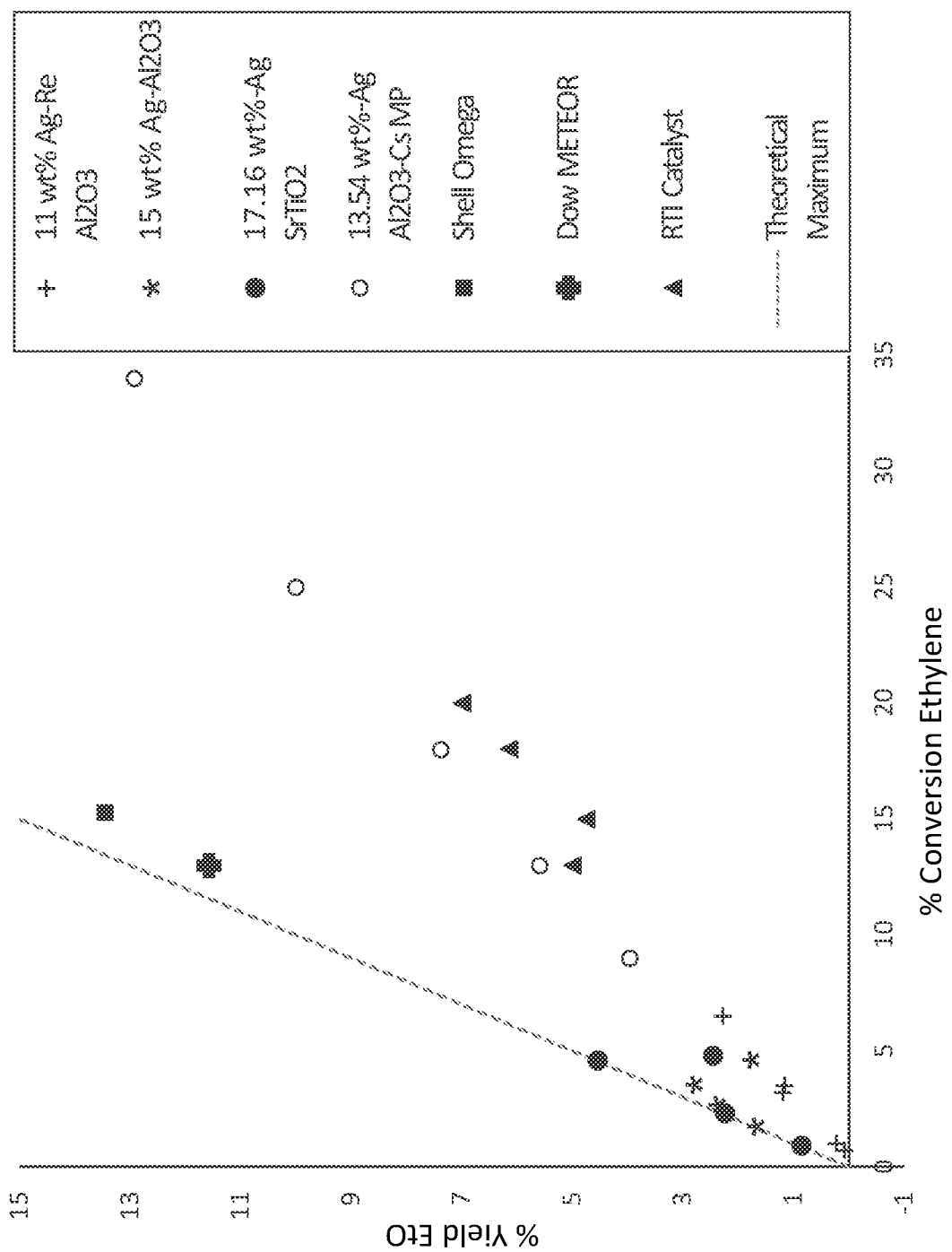

The $CO_2$ utilization catalysts show higher conversion of ethylene than most of the conventional catalysts. They are less selective than the best conventional catalysts, however given the conversions, the yields compare favorably to some of the conventional catalysts, as is illustrated in FIG. 2.

$CO_2$-Utilizing Catalyst Formulations

The transfer of oxygen from carbon dioxide to ethylene is made possible only by the combination of specific metal oxide phases on the surface of the catalysts disclosed herein. The important phases are combinations of molybdenum trioxide and ruthenium oxide, or molybdenum trioxide and silver oxide. The catalysts have been characterized by powder x-ray diffraction spectroscopy and x-ray fluorescence spectroscopy. The metal oxide phases are supported on conventional heterogeneous catalyst supports. Various supports such as silica, titania, zirconia, and alumina have been tested and shown to be useful when combined with the specified catalyst phases, however supports of alumina show the highest levels of ethylene oxide production when combined with the specified catalyst phases. The alumina supports can be either gamma-, alpha-, or any other phase of alumina, however gamma- and alpha- show the most promising levels of production.

Preliminary results indicate that the catalysts composed of mixtures of ruthenium oxides and molybdenum oxides combined in a ratio of three moles molybdenum to one mole ruthenium perform optimally. However, many other ratios of molybdenum to ruthenium have been demonstrated to work for the production of ethylene oxide from $CO_2$ and ethylene. The molar ratio of ruthenium oxides to molybdenum oxides can be approximately 1:50, 1:40, 1:30, 1:20, 1:10, 1:9, 1:8, 1:7, 1:6, 1:5, 1:4, 1:3, 1:2, 1:1. Molybdenum oxide does not necessarily have to be the higher of the two concentrations, and the molar ratio of molybdenum oxide to ruthenium oxide can be 1:50, 1:40, 1:30, 1:20, 1:10, 1:9, 1:8, 1:7, 1:6, 1:5, 1:4, 1:3, 1:2, 1:1. Common inorganic salts are satisfactory precursor materials for formation of the catalysts Ammonium molybdate has been used as the primary source of molybdenum for the catalysts. Ruthenium chloride and ruthenium nitrosylnitrate have been utilized as inorganic sources of ruthenium. However other molybdenum containing or ruthenium containing reagents could be used as starting materials, and the invention covers any satisfactory molybdenum- or ruthenium-containing starting material.

An exemplary catalyst composition, as determined by X-ray fluorescence (XRF), is $RuO_2(MoO_3)_3(Al_2O_3)_{22}$, and the mole ratio of molybdenum to ruthenium is approximately 3:1. Results from XRF, along with the theoretical values based on the empirical amount of starting materials, are presented in the table below. The detection of titanium is an impurity that is not intended to be part of the catalyst formulation.

TABLE 2

XRF Results of a $RuO_2(MoO_3)_3(Al_2O_3)_{22}$ Catalyst

| Wt % Analysis Sample ID | Mass (mg) | Aluminum Calc. (% Wt.) | Molybdenum Calc. (% Wt.) | Ruthenium Calc. (% Wt.) | Titanium Calc. (% Wt.) | Chlorine |
|---|---|---|---|---|---|---|
| RTI-Al$_2$O$_3$ | 134.367 | 42.073 | 14.613 | 4.220 | 0.123 | 0 |
| Theory | | 42.278 | 10.250 | 3.599 | 0 | 0 |

Figure 3:
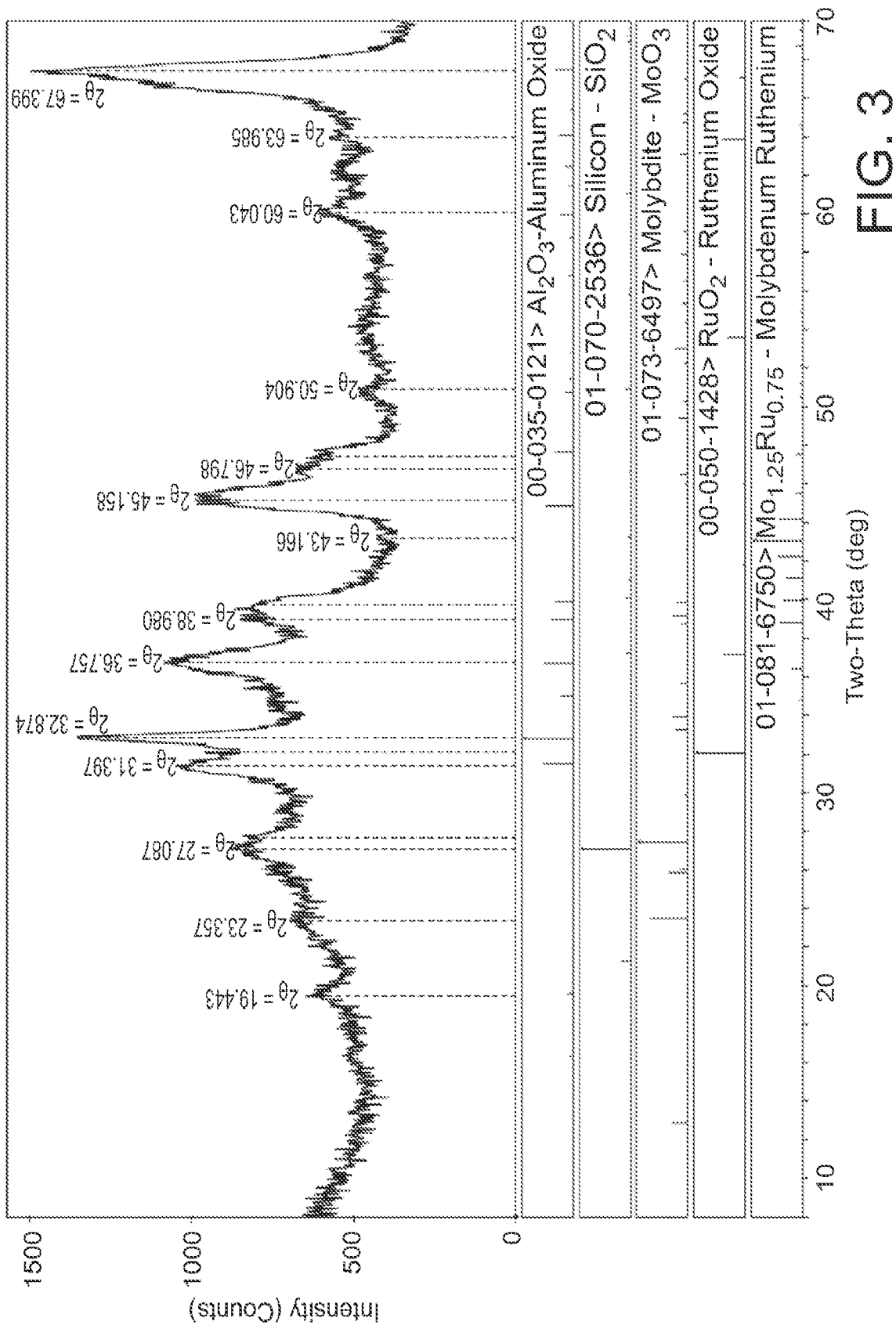

The X-ray diffraction (XRD) spectrum of the catalyst is shown in FIG. 3. The XRD revealed that this sample is not highly crystalline, probably because of the low calcination temperature or relatively short aging period that was used during synthesis. The catalyst specified in the example was calcined at 350° C. (~625° K), but working catalysts can be obtained by calcination at 300° C., 325° C., 350° C., 375° C., 400° C., 425° C., 450° C., 475° C., 500° C., 525° C., 550° C., 575° C., 600° C., 625° C., 650° C., 675° C., and 700° C. Calcination temperature can have a noticeable impact on the catalyst activity. Mild calcination conditions can maintain small crystallite size and thorough dispersion of the catalyst on the support surface. The XRD shown in FIG. 3 is consistent with this scenario. However, some heterogeneous catalysis are optimized when the crystal size of specific phases are larger. Generally, the crystal size grows as the calcination temperature is increased or as the aging temperature is lengthened, and this is one aspect of the current catalyst that can be varied to purposefully obtain specified levels of activity.

The phases that are detected by XRD in the specific example are the common oxide phases of the metals used in the preparation. In this particular example, $Al_2O_3$ is the predominant phase as expected for the supported catalyst. A high purity, high surface area γ-alumina was used as the support material. $MoO_3$ is the primary phase detected for molybdenum, and $RuO_2$ is the primary phase of ruthenium in the catalyst. An alloy of molybdenum and ruthenium could also be present in the sample based on this analysis. $SiO_2$ is likely not present in any substantial amount, but it could be present as a small impurity in starting materials, but silicon was not detected by XRF.

Figure 4:
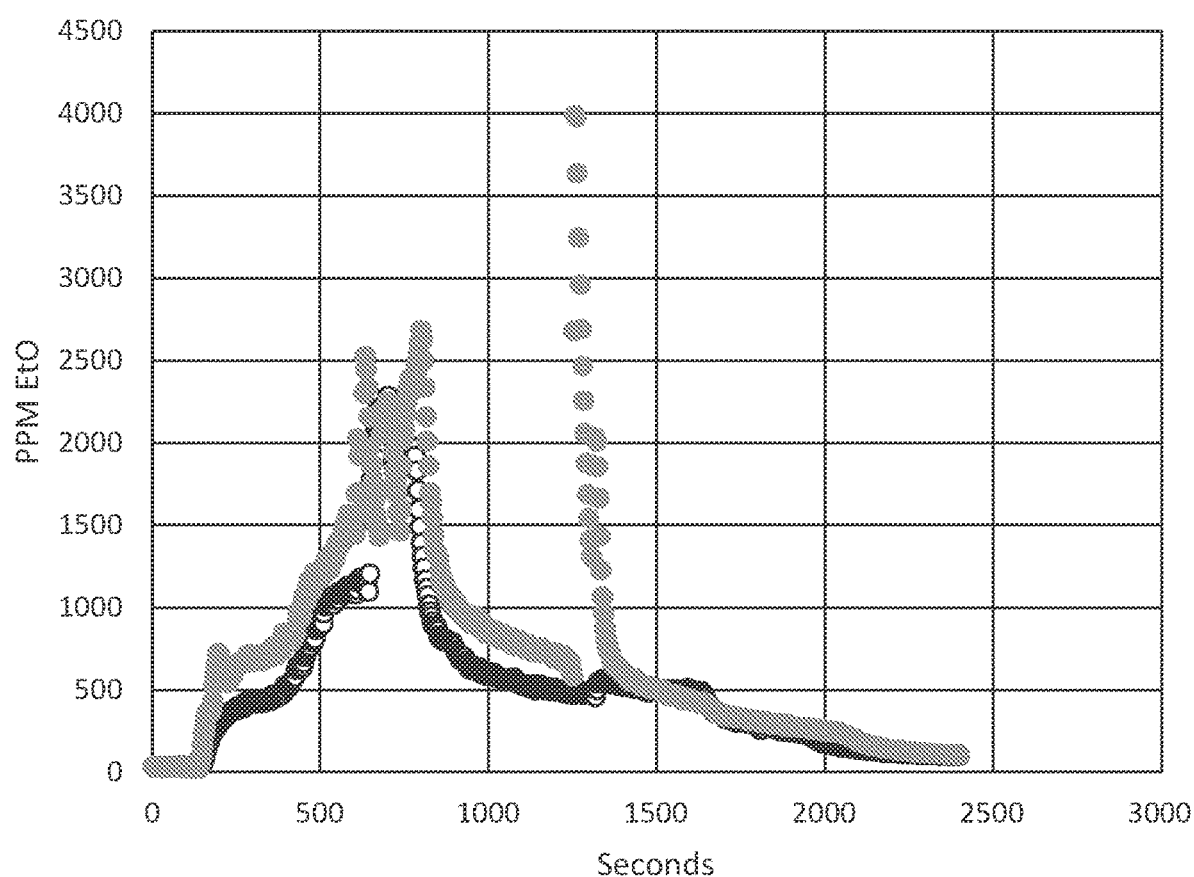

When the catalyst is exposed to a feed gas stream containing carbon dioxide and ethylene, the catalyst produces a product stream containing ethylene oxide and carbon monoxide. The feed gas stream does not contain molecular oxygen, and the only sources of atomic oxygen in the feed stream are the metal oxides in the catalysts along with carbon dioxide. When the catalyst surface is contacted with ethylene and $CO_2$, ethylene oxide is observed in the product stream. FIG. 4 shows the reactivity of the catalyst towards ethylene and $CO_2$ when the catalyst is exposed to the feed mixture for approximately forty minutes. At the start of the experiment the amount of ethylene oxide produced is low, presumably due to a period of time required for the reactants to absorb to the catalyst surface. After approximately 500 seconds the reactants begin to combine and the concentration of ethylene oxide in the product stream rises to approximately 500 ppm. The concentration of ethylene oxide then rises and is sustained between 1500 and 2500 ppm and is maintained at this level for approximately five minutes. The level of ethylene oxide in the product stream then decreases to approximately 500 ppm and is maintained there for thirty minutes before gradually decreasing to below 100 ppm. The gradual decrease in activity is presumably due to carbon buildup on the catalyst surface which can be removed in a subsequent oxidation step to regenerate the catalyst surface.

Figure 5A:
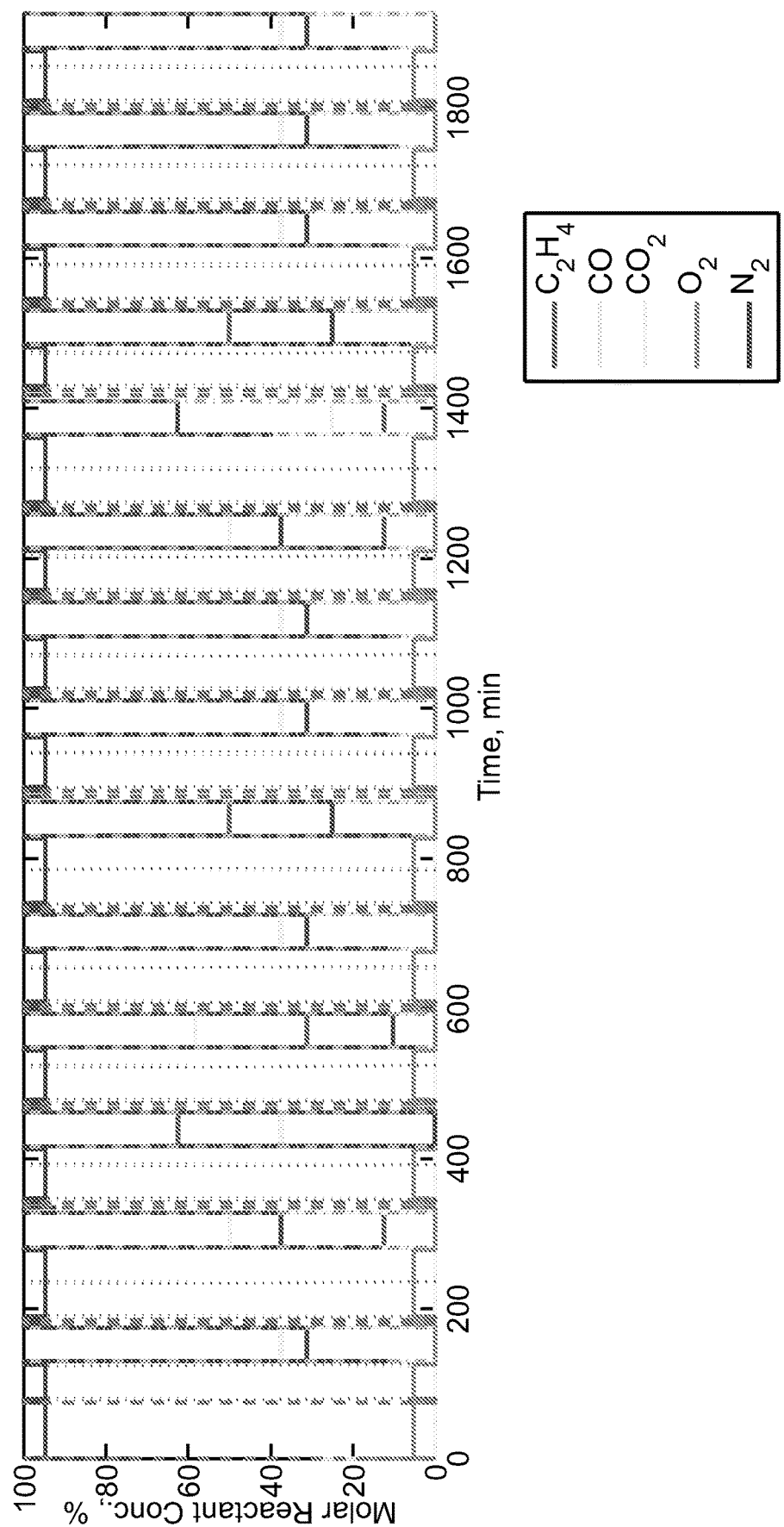
FIG. 5A-FIG. 5C show the $RuO_2(MoO_3)_3(Al_2O_3)_{22}$ catalyst in a cofeed mode of operation to produce ethylene oxide.
Figure 5B:
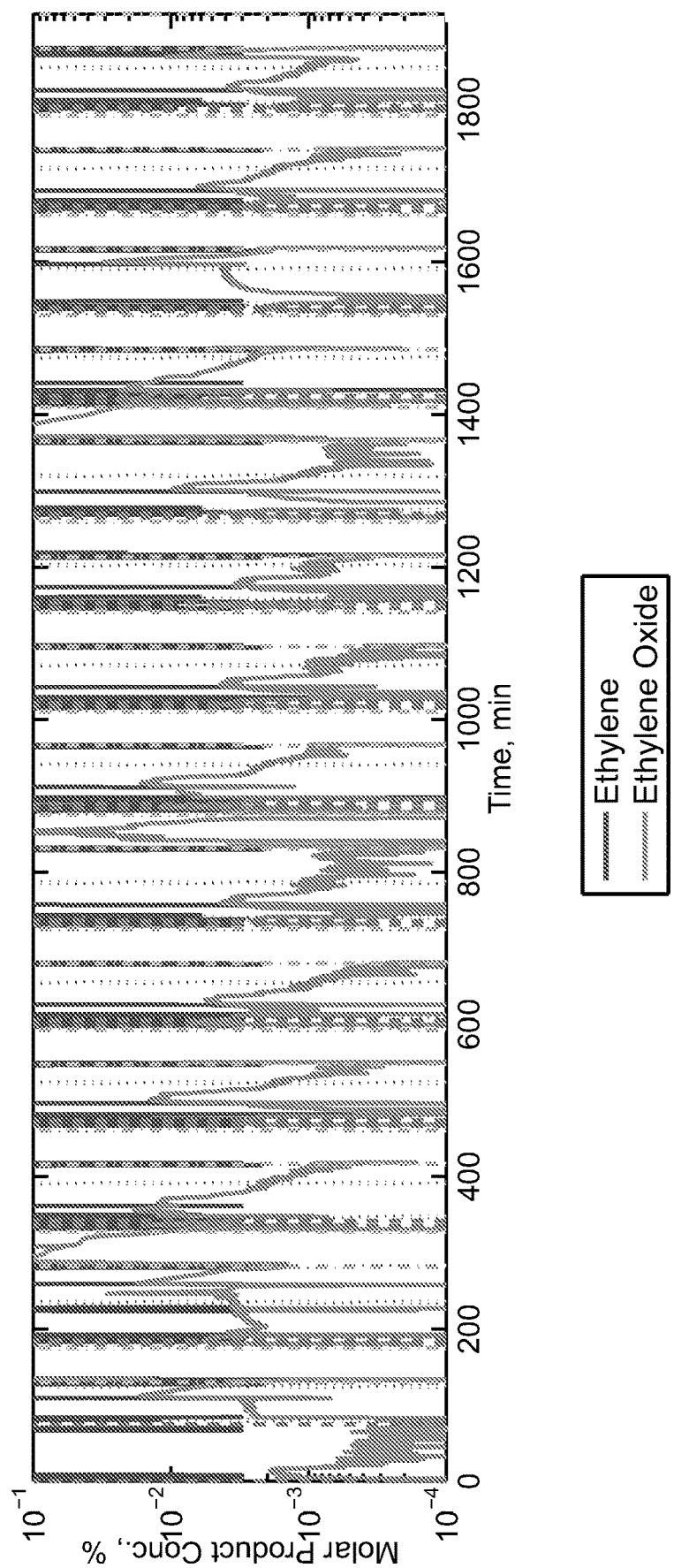
Figure 5C:
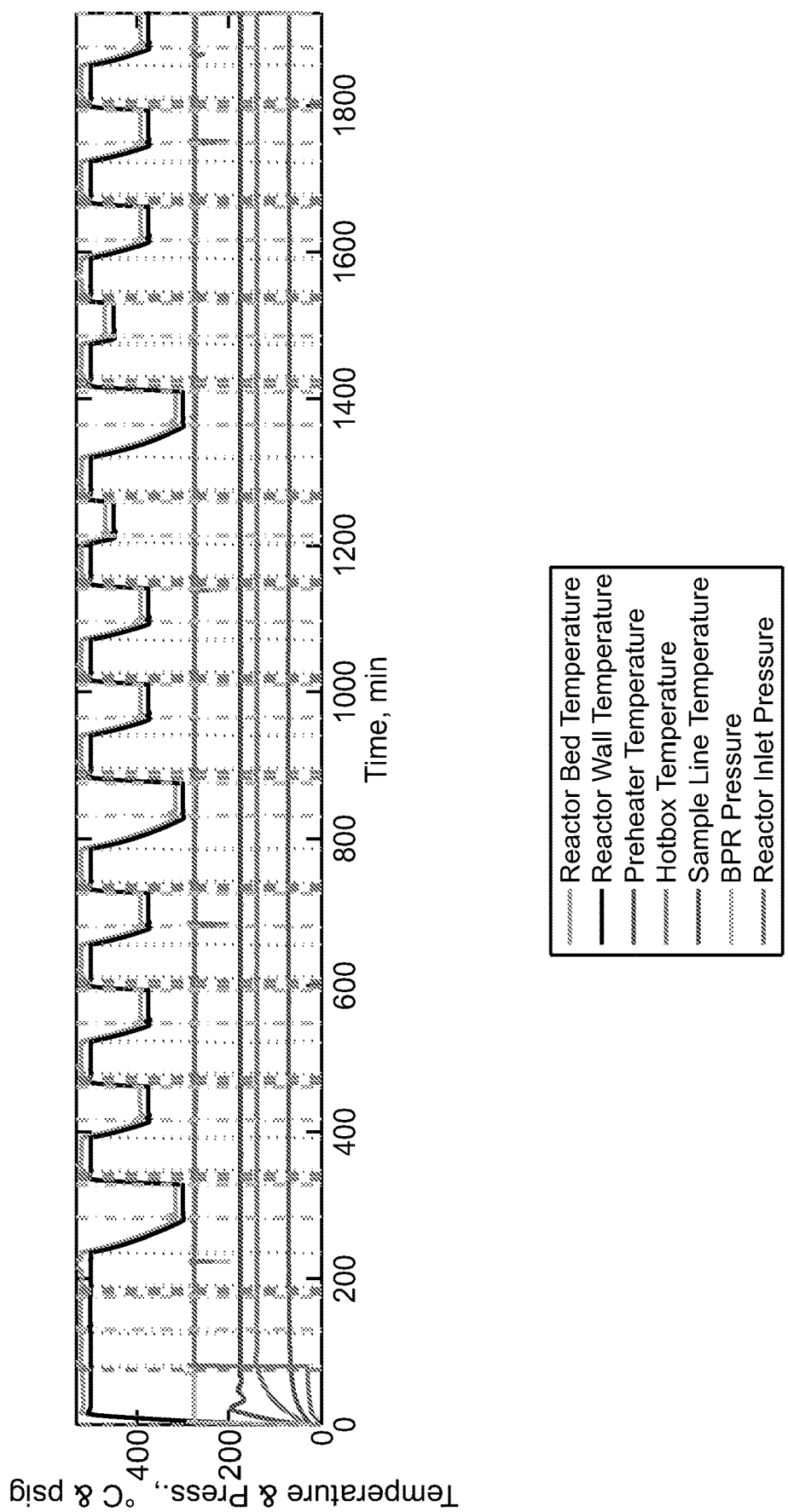

FIG. 5A-FIG. 5C shows the catalyst operated under various conditions and shows the catalyst ethylene oxide production levels in FIG. 5B. The reactor feed stream compositions are shown in FIG. 5A and temperature and pressure conditions are shown in FIG. 5C. FIG. 5A-FIG. 5C shows that the catalyst can be treated in a co-feed mode of operation to produce ethylene oxide. In the co-feed mode of operation $CO_2$ and ethylene are fed simultaneously to the catalyst to produce ethylene oxide in a mixed product stream containing CO. In alternative mode, the catalyst is treated sequentially by exposing the catalyst to $CO_2$ where an oxygen is removed from $CO_2$ to produce CO. In the next step, the catalyst is exposed to ethylene to produce ethylene oxide.

The catalysts which utilize the combination of silver and molybdenum are described below. Combinations of silver and molybdenum oxides are also effective for catalyzing the transfer of oxygen from $CO_2$ to alkenes. The molar ratio of molybdenum to silver can be approximately 1:1, 1:2, 1:3, 1:4, 1:5 or the catalyst can be formulated with a higher concentration of molybdenum with molar ratio of molybdenum to silver of 5:1, 4:1, 3:1, or 2:1.

An exemplary catalyst composed of silver and molybdenum oxides is described below. The catalyst was prepared by composing a solution of 0.0459 moles silver nitrate and 0.1001 moles aluminum nitrate in seventy-five mLs water. Another solution was made by dissolving 0.0065 moles ammonium heptamolybate in seventy-five mLs water. The two solutions were combined and the resulting solution pH was raised by adding ammonium hydroxide until the solution pH was >8. The resulting solid was filtered, washed, dried, then calcined at 550° C. for 3.0 hours.

Figure 6:
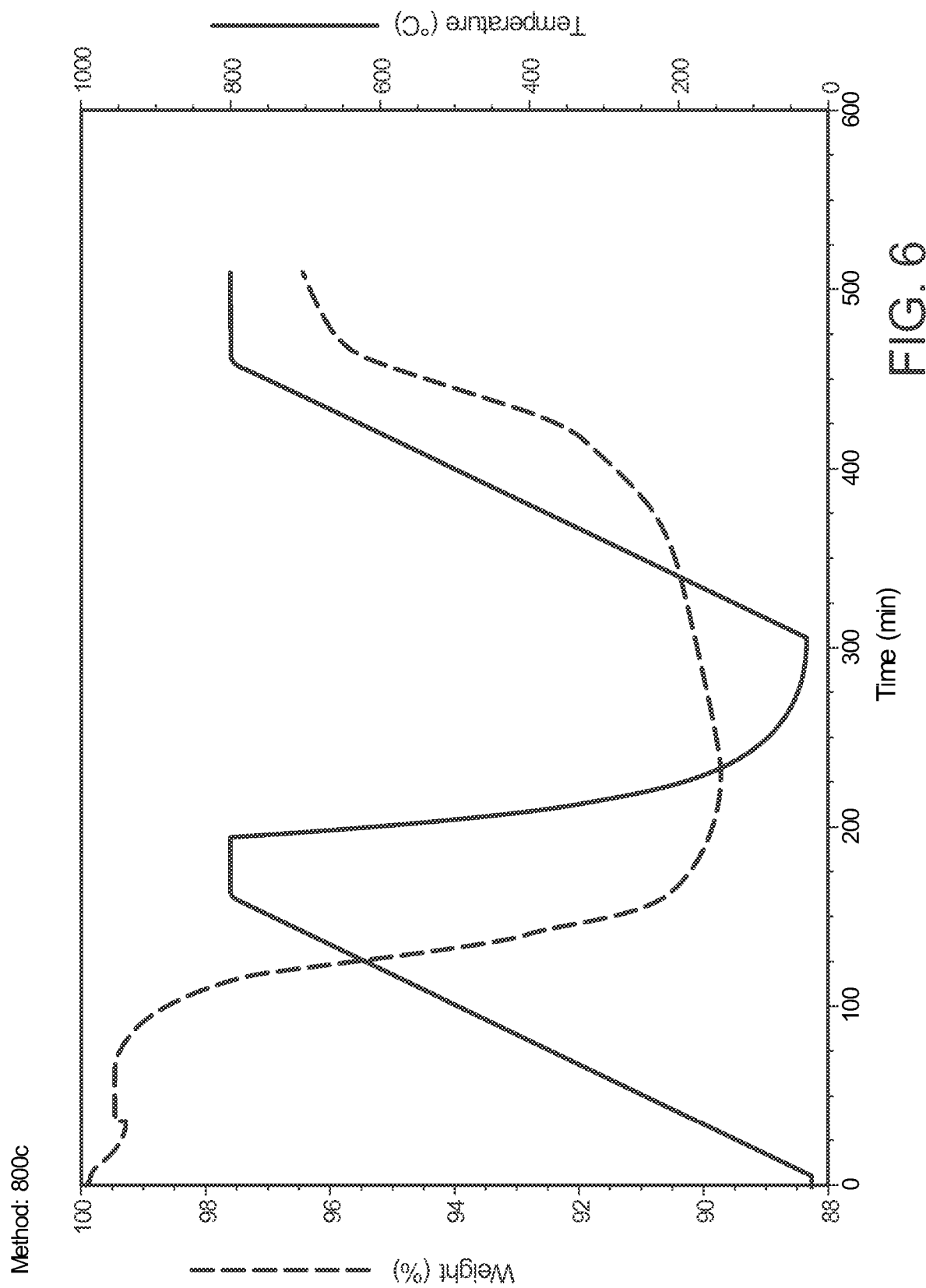
FIG. 6 shows thermogravimetric analysis (TGA) of the catalyst $((Ag_2O)(MoO_3)_2(Al_2O_3)_2$ catalyst).

FIG. 6 demonstrates the redox behavior of the catalyst and shows the efficacy of the catalyst towards abstraction of oxygen from $CO_2$. In FIG. 6, the dashed line is the weight % profile (left Y axis) and the black solid line is the temperature profile (right Y axis). Thermogravimetric analysis is used to show the gravimetric behavior of the catalyst $((Ag_2O)(MoO_3)_2(Al_2O_3)_2)$ catalyst after a reductive step followed by exposure to $CO_2$. Carbon monoxide is flowed over the catalyst during the reductive step (first 200 minutes of the experiment) to affect a weight loss of more than 10 wt %. During this time the catalyst is heated from ambient temperature to 800° C. The weight loss is due to loss of oxygen from the metal oxide and conversion of CO to $CO_2$, indicative of the catalyst being reduced. The sample is then cooled back to near ambient temperature and the gas is switched to carbon dioxide. As a result, the mixed-metal oxide begins to gain weight, and as the temperature is elevated the sample gains approximately 8 wt % due to the transfer of oxygen from carbon dioxide to the catalyst.

Figure 7A:
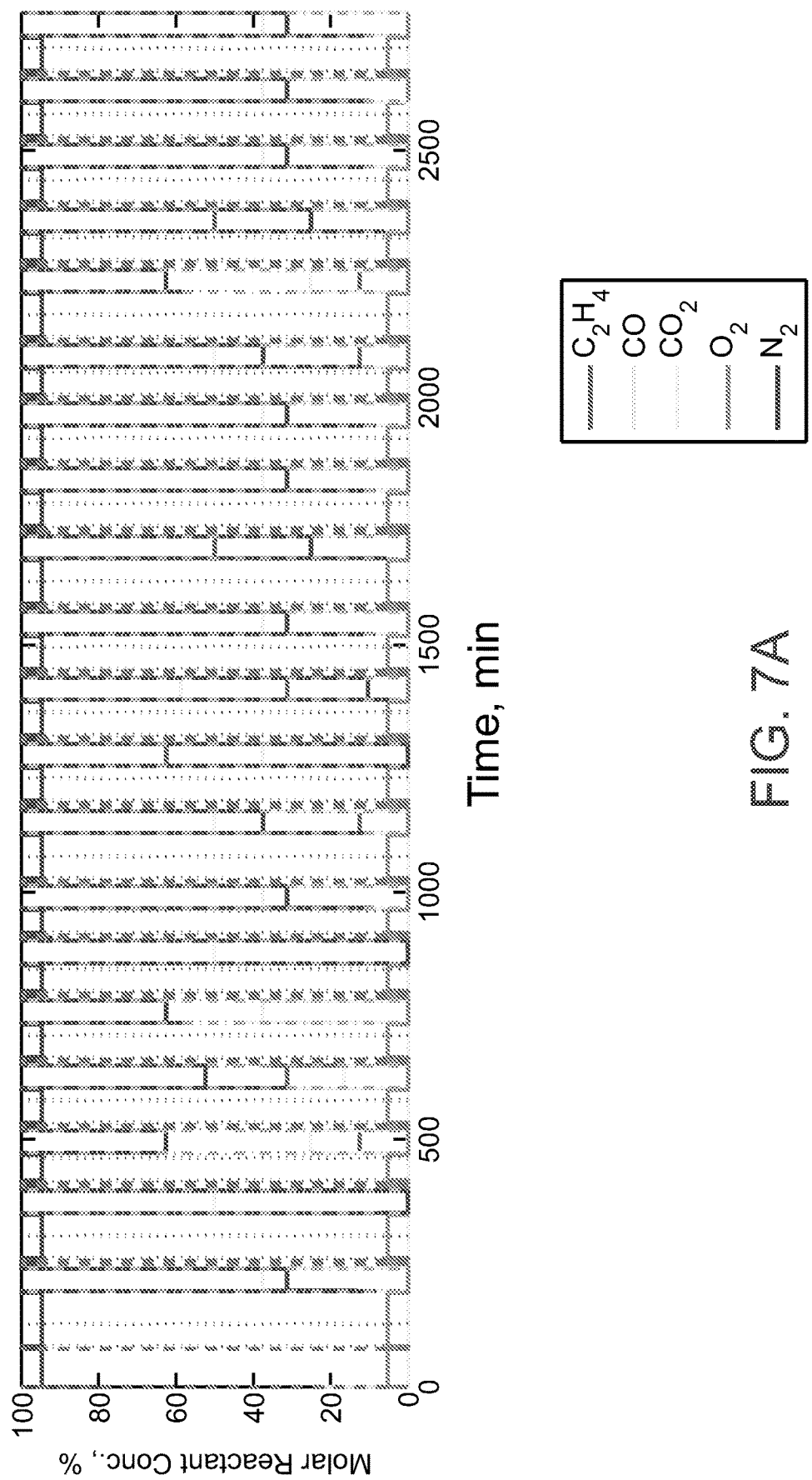
FIG. 7A-FIG. 7C show the $(Ag_2O)(MoO_3)_2(Al_2O_3)_2$ catalyst in a cofeed mode of operation to produce ethylene oxide.
Figure 7B:
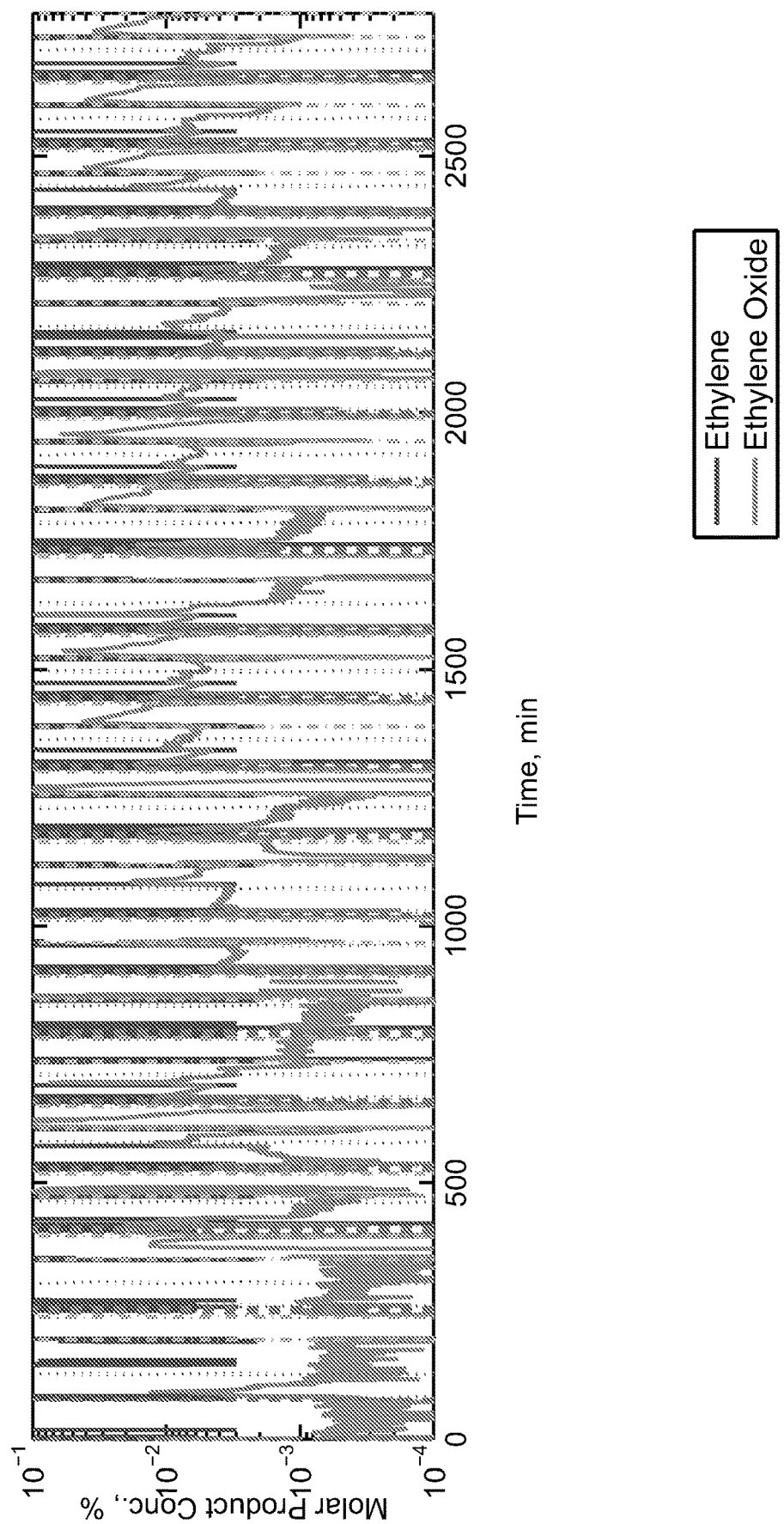
Figure 7C:
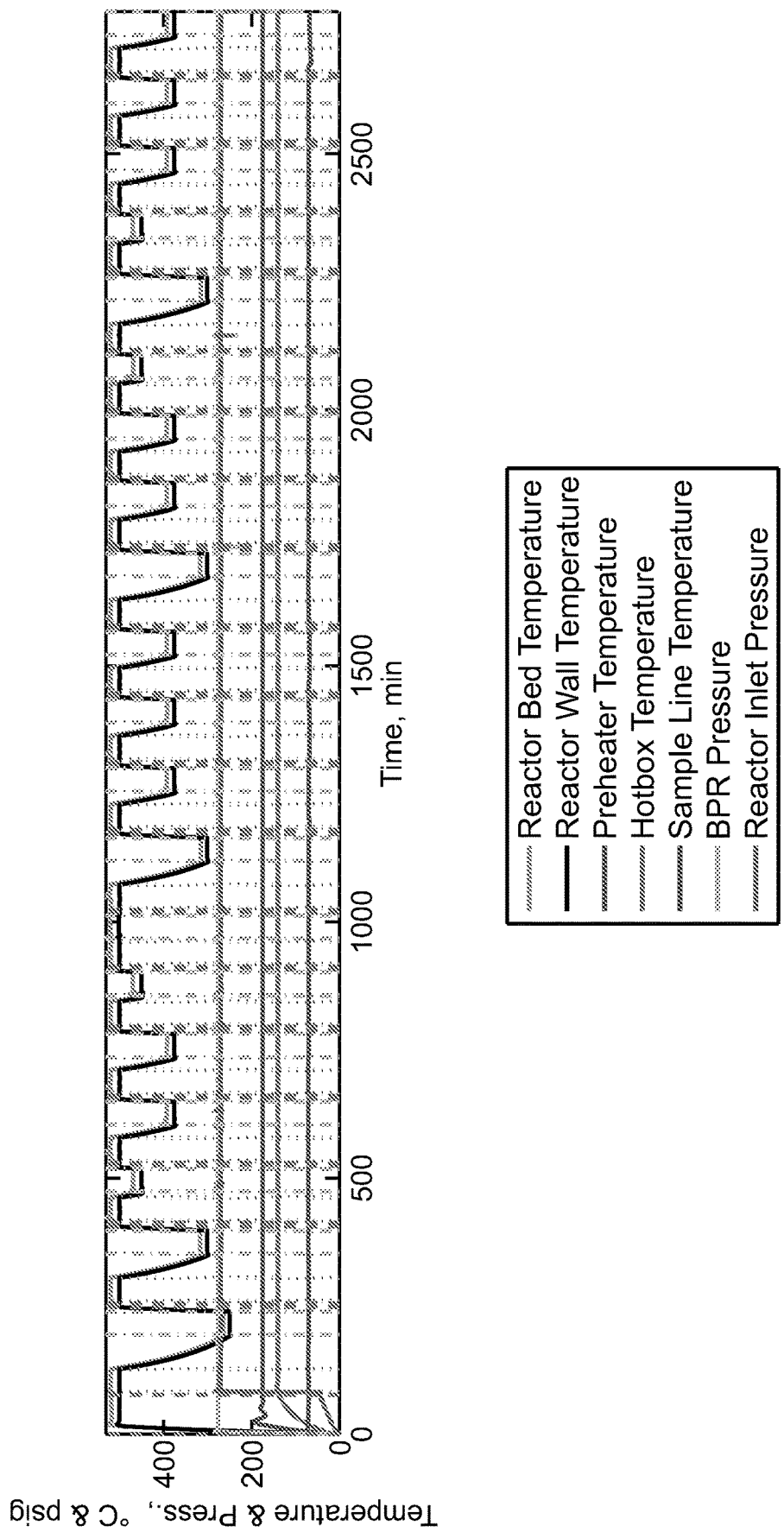

FIG. 7A-FIG. 7C shows the catalyst composed of silver and molybdenum oxides tested under $CO_2$ and ethylene flow under varying process parameters and demonstrates that the catalyst produces ethylene oxide (FIG. 7B). Ethylene oxide is detected by infrared spectrum using a multigas analyzer. The reactor feed stream compositions are recorded in the top graph and temperature and pressure conditions are shown in the bottom graph. FIG. 7A-FIG. 7C shows that the catalyst can be treated in a co-feed mode of operation to produce ethylene oxide. In the co-feed mode of operation $CO_2$ and ethylene are fed simultaneously to the catalyst to produce ethylene oxide in a mixed product stream containing CO. In alternative mode, the catalyst is treated sequentially by exposing the catalyst to $CO_2$ where an oxygen is removed from $CO_2$ to produce CO. In the next step, the catalyst is exposed to ethylene to produce ethylene oxide.

The combination of molybdenum, silver, and ruthenium can also be used to transfer oxygen from carbon dioxide to alkenes to make epoxides. As an exemplary formulation, a catalyst was synthesized by combining 0.0046 moles ammonium heptamolybdate and 0.0059 moles silver nitrate in approximately 20 mL water. To this homogeneous solution, 10 grams of SBA-15 mesoporous silica was added to make a slurry. Water was removed from the slurry by rotary evaporation and the powder was set aside. In a separate solution, 0.0019 moles ruthenium chloride was dissolved in 10 mL water. The catalyst powder from the first solution was milled and dried then the aqueous ruthenium chloride solution was added to the powder with thorough mixing and dispersion. After all the solution was added the powder was further dried by rotary evaporation, then dried at 120° C. followed by calcination at 350° C.

Figure 8:
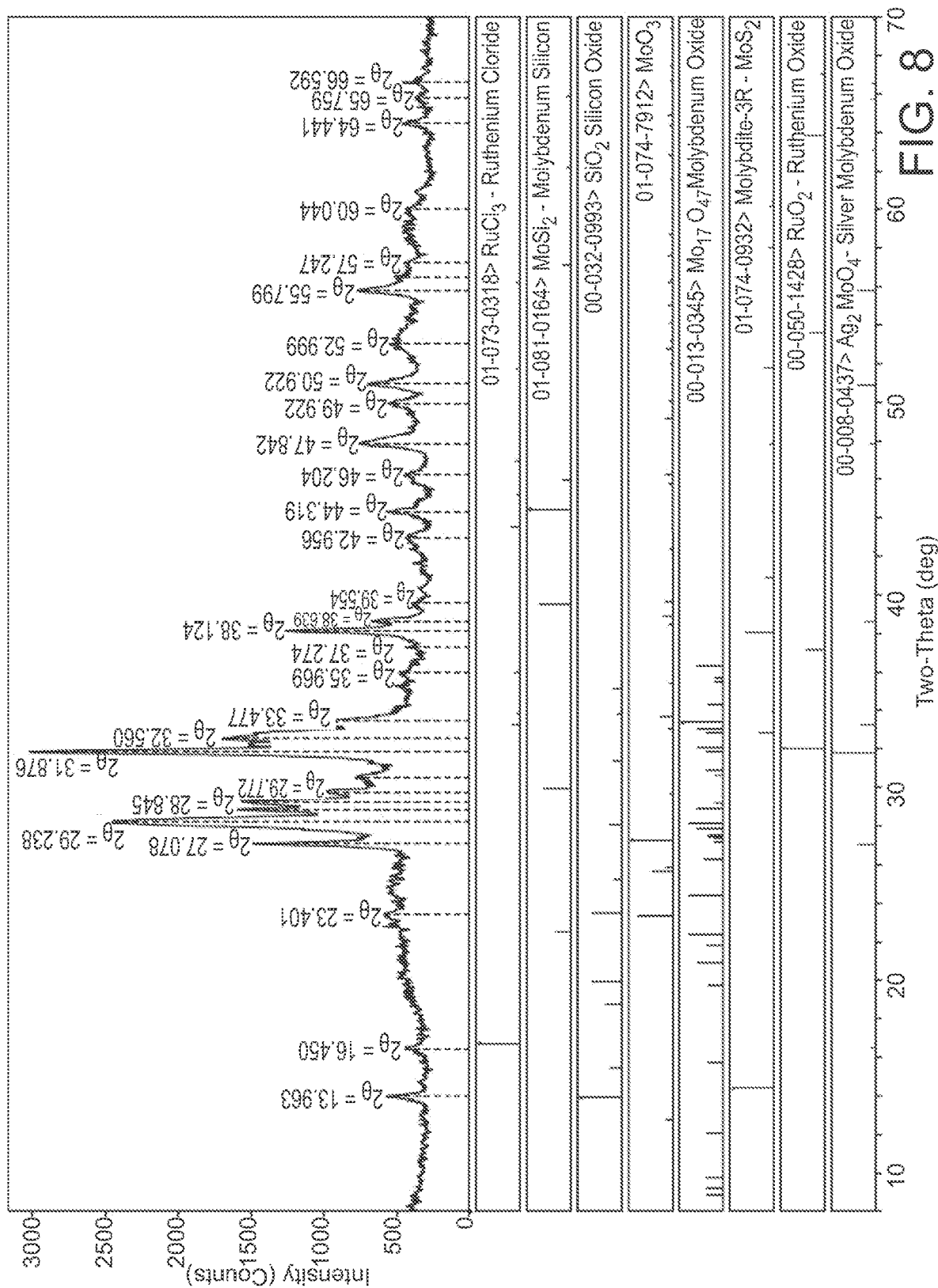
FIG. 8 shows XRD analysis of $AgRuMoSiClO_x$ catalyst used for $CO_2$-ethylene epoxidation.

The XRF and XRD analyses of the material are shown in Table 3 and FIG. 8.

TABLE 3

Compositional analysis by XRF of $AgRuMoSiClO_x$ catalyst used for $CO_2$-ethylene epoxidation.

| Wt % Analysis Sample ID | Mass (mg) | Si Calc. (% Wt.) | Ag Calc. (% Wt.) | Mo Calc. (% Wt.) | Ru Calc. (% Wt.) | Cl Calc. (% Wt.) |
|---|---|---|---|---|---|---|
| $AgRuMoSiClO_x$ | 124.533 | 31.627 | 18.723 | 11.273 | 0.436 | 0.304 |

XRF confirms the presence of silver, ruthenium, and molybdenum on the mesoporous silica support. The material contains chlorine which is known to those of skill in the art to have positive impact on ethylene oxide catalysts which depend on molecular oxygen rather than $CO_2$. The use of ruthenium chloride or other chloride salts as starting material, along with calcination temperatures, can be tuned to intentionally modify the amount of chloride in the catalyst.

FIG. 8 shows the resulting XRD pattern of the obtained $AgRuMoSiClO_x$ powder.

There are several phases present in the material including ruthenium chloride, molybdenum trioxide, silicon dioxide, ruthenium oxide, and silver molybdenum oxide.

Figure 9A:
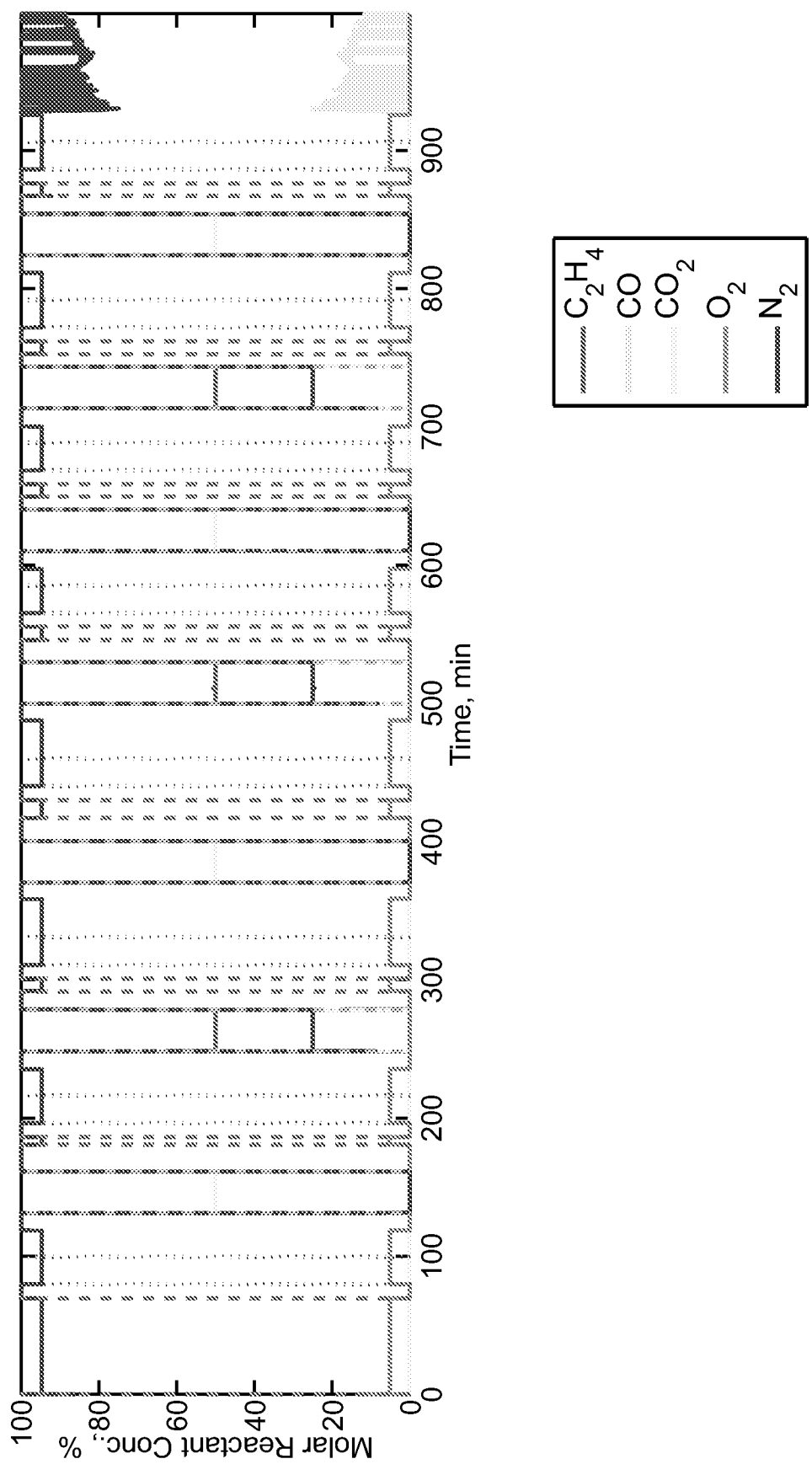
FIG. 9A-FIG. 9C show that the $AgRuMoSiClO_x$ catalyst in a cofeed mode of operation to produce ethylene oxide.
Figure 9B:
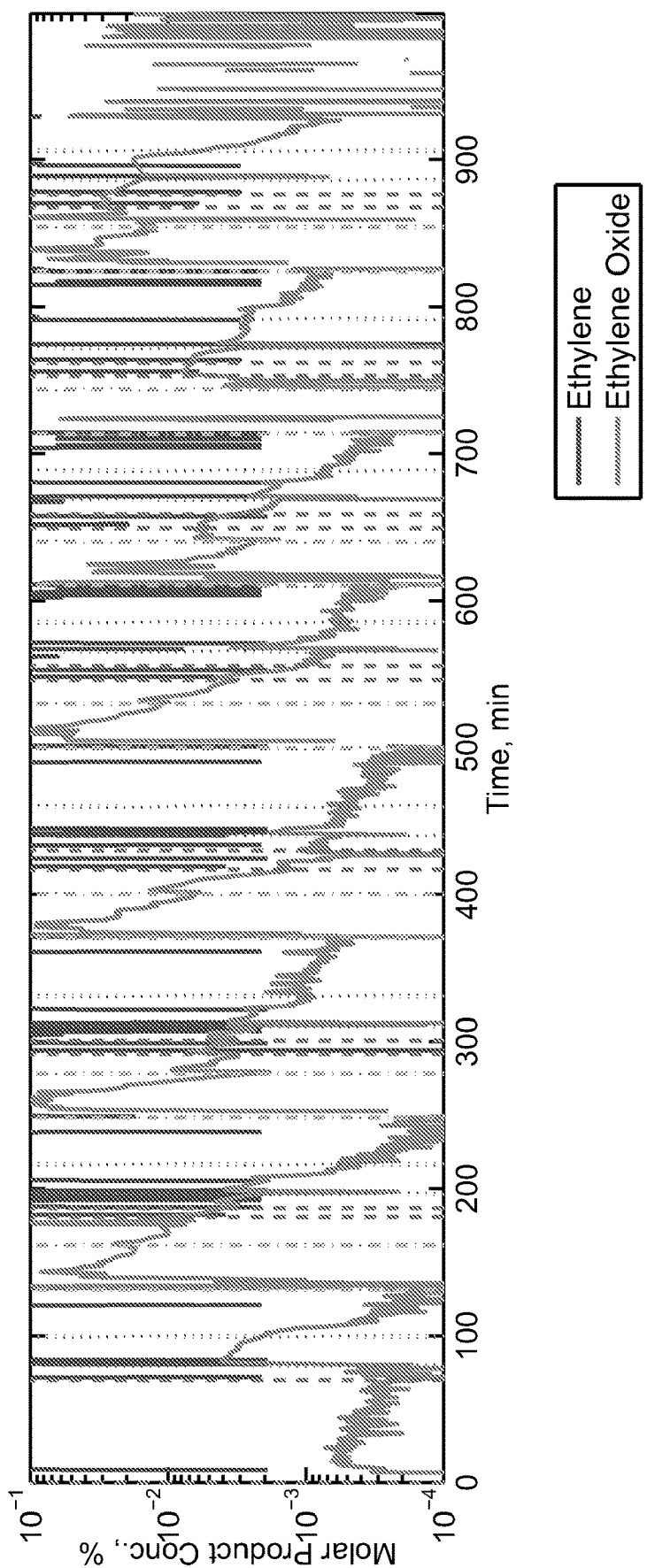
Figure 9C:
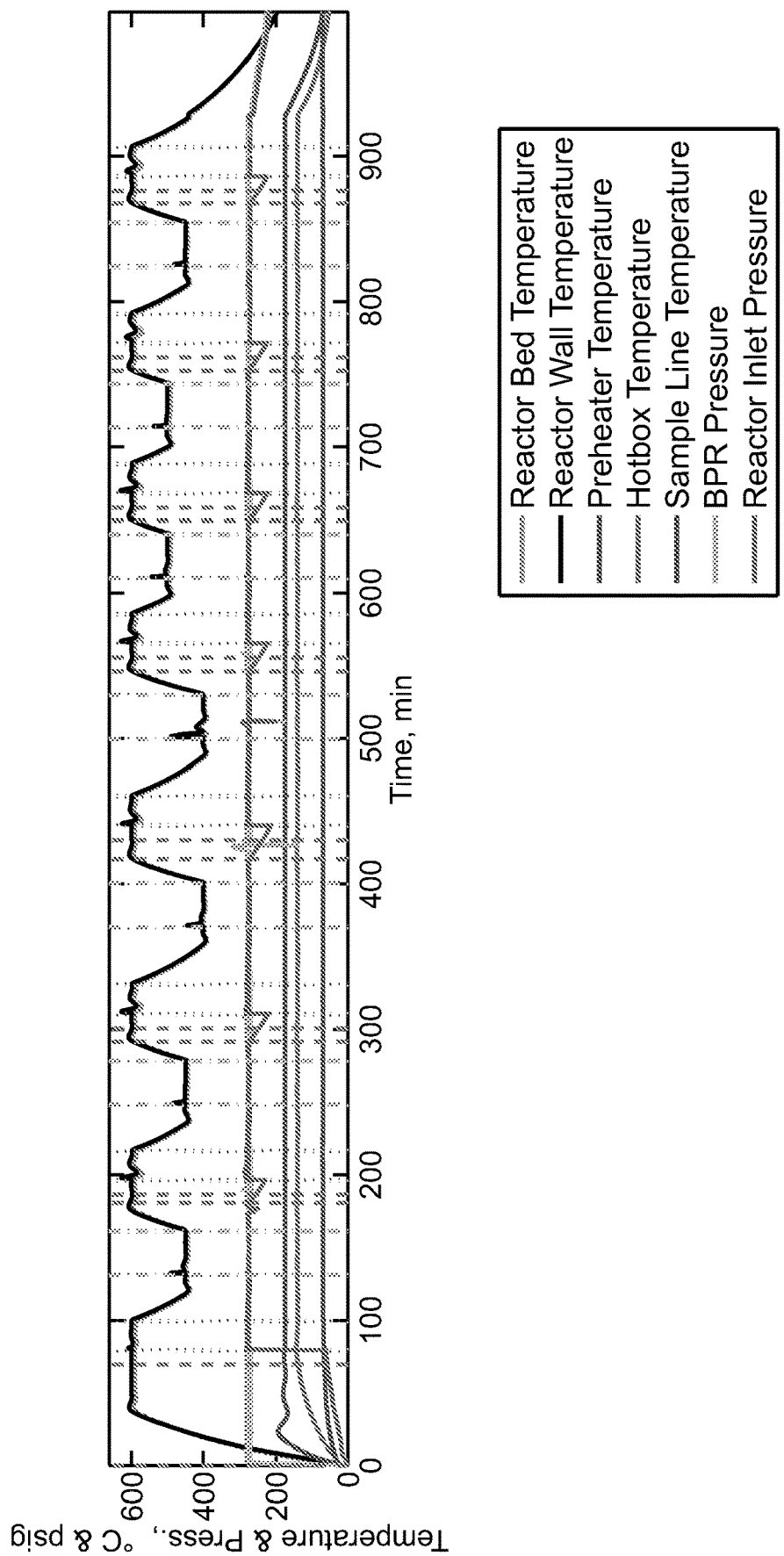

FIG. 9A-FIG. 9C shows the $AgRuMoSiClO_x$ catalyst in the presence of $CO_2$ and ethylene feed-gas mixture flowing under a dynamic series process parameters and demonstrates that the catalyst produces ethylene oxide (FIG. 9B, IR signal from multi-gas analyzer. The reactor feed stream compositions are recorded in the upper graph and temperature and pressure conditions are shown in the lowest graph. FIG. 9A-FIG. 9C shows that the catalyst can be treated in a co-feed mode of operation to produce ethylene oxide. In the co-feed mode of operation $CO_2$ and ethylene are fed simultaneously to the catalyst to produce ethylene oxide in a mixed product stream containing CO. In alternative mode, the catalyst is treated sequentially by exposing the catalyst to $CO_2$ where an oxygen is removed from $CO_2$ to produce CO. In the next step, the catalyst is exposed to ethylene to produce ethylene oxide.

The catalysts described above can be prepared by a number of conventional heterogeneous catalyst preparation routes, including but not limited to, wet deposition, co-precipitation, and incipient wetness impregnation. Two exemplary methods for preparing the catalysts are described below: wet deposition and co-precipitation. Each preparation method has merit. Wet deposition has the merit of concentrating all of the active catalyst phase on the surface of the support, but it does not have as many phase interfaces, which could be important to the catalysis. Co-precipitation has more phase interfaces, but it could lead to some of the catalyst phases being in the bulk of the material and not exposed to the surface where gas-solid interactions take place.

Wet deposition is a catalyst preparation method during which the surfaces of inert support materials such as alumina ($Al_2O_3$) or silica ($SiO_2$) are doped with small amounts of transition-metals. The transition-metals are deposited on the surface of the support as decomposable inorganic salts. After deposition, the inorganic salts are calcined at a high temperature (between 300° C. and 550° C.) to make the transition-metal oxide, or mixed-metal oxides, when more than one transition metal is used. An advantage of using a wet deposition preparation is that the active catalyst materials are concentrated at the surface of the catalyst rather than elsewhere in the bulk. A preparation of molybdenum-impregnated alumina is provided here as an example. In a round-bottomed flask with a ground-glass neck, 3.5 g of ammonium molybdate was dissolved in 20 mL of $H_2O$. A gravimetric balance was used to weigh out 15 g of γ-alumina, and then the alumina was added to the round-bottomed flask containing the molybdenum solution. $H_2O$ was added to completely cover the alumina. A rotary evaporator was used to remove the $H_2O$ from the solution. When the sample was air dried, calcination was performed by heating the solid at 120° C. for 2 hours to 350° C. at a 5° C. per minute ramp rate and holding for 3 hours to obtain 16.6 g of powder. This approach was used to prepare the most promising catalysts.

Co-precipitation is a catalyst preparation method during which an aqueous solution of metal salts is created, typically containing more than one metal salt, followed by adding an aqueous base to the solution, which raises the pH of the aqueous solution, resulting in precipitation of the metal species in solution as insoluble metal hydroxides. The species often precipitate together and form solids that are filtered from the solution, are dried, and then are calcined to convert the metal hydroxides into the corresponding metal oxides. A preparation of a silver molybdate mixed-metal oxide by co-precipitation is given as an example. In a beaker, 19.33 g of silver nitrate and 37.4 g of aluminum nitrate were combined, and then dissolved these in 75 mL of $H_2O$. In another beaker, 8.01 g of ammonium heptamolybdate was dissolved in approximately 25 mL of $H_2O$. With a Pasteur pipette, the ammonium heptamolybdate solution was added to the silver-aluminum solution. The pH was tested after all of the solution was added, and then ammonium hydroxide was added to the solution until the pH was greater than 8. Next, the solid precipitate was filtered and washed thoroughly by using number 1 filter paper. After the solid precipitate was air dried, it was further dried and calcined it by heating the solid at 120° C. for 2 hours, and then heating it to 550° C. at a 5° C. per minute ramp rate. The temperature was held constant for 3 hours, obtaining 6.45 g of calcined powder.

Disclosed herein are several catalysts that can be used for ethylene epoxidation using $CO_2$ instead of $O_2$. The catalysts react with $CO_2$ and remove an oxygen atom to produce EtO and carbon monoxide (CO), which is a feedstock for many value-added chemicals. The general reaction scheme using the catalyst as a chemical-looping agent is shown below. The two marketable product streams from the proposed process are EtO and CO, which are both valuable intermediates for the established Alberta petrochemical industry.

$CO_2$ reduction: $CO_2 + M^0 \rightarrow CO + MO$ (Eq. 1)

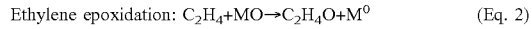
Ethylene epoxidation: $C_2H_4 + MO \rightarrow C_2H_4O + M^0$ (Eq. 2)

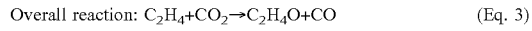
Overall reaction: $C_2H_4 + CO_2 \rightarrow C_2H_4O + CO$ (Eq. 3)

[$M^0$=Reduced metal; MO=Metal oxide]
General Reaction Scheme for $CO_2$ Utilization Approach for Et Oxidation.

In one embodiment, the reactions occur in a co-feed reactor, here both of the main reactants, $CO_2$ and Et, are fed together into the main reactor where the epoxidation and reduction reactions listed above occur sequentially in the same reactor. The overall reaction is slightly endothermic. An example of a process flow diagram of the technology is shown in FIG. 10. The process models were developed to depict the overall process to produce 250,000 tons/yr of EtO.

In the process, Et and $CO_2$, after heating and expansion from pipeline pressures, are mixed and heated to the reactor temperature. Additional external heat is supplied to the reactors to provide the heat required for the reactions to take place. The co-feed reactor was assumed to be isothermal in the process model, and the heat duty of the reactor was considered in the GHG life-cycle analysis (LCA) to estimate the cost of the thermal energy requirement for this process.

The feed mixture is sent to the co-feed reactor, where the oxidation and reduction reactions take place over the metal catalyst to produce CO and EtO. Similar to the commercial process, the undesirable side reaction (see the equations below) in which Et is completely oxidized to form $CO_2$ and water were found to be inevitable. The oxygen for oxidation comes from $CO_2$, so the process ends up as endothermic and a large consumer of $CO_2$, however, at the expense of the valuable Et feedstock. As a result, this side reaction must be kept at a minimum to keep the techno-economics of the process favorable.

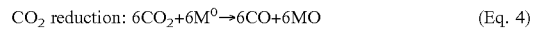
$CO_2$ reduction: $6CO_2 + 6M^0 \rightarrow 6CO + 6MO$ (Eq. 4)

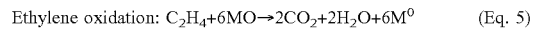
Ethylene oxidation: $C_2H_4 + 6MO \rightarrow 2CO_2 + 2H_2O + 6M^0$ (Eq. 5)

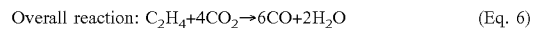
Overall reaction: $C_2H_4 + 4CO_2 \rightarrow 6CO + 2H_2O$ (Eq. 6)

[$M^0$=Reduced metal; MO=Metal oxide]
General reaction scheme of the Et oxidation side reaction.

The technology disclosed herein is compared to the conventional method for producing EtO. The block diagram of the conventional EtO manufacturing process is shown in FIG. 11. In the conventional process, Et and $O_2$ are mixed and are passed over a catalyst consisting of $Ag_2O$.

The $O_2$ stream is produced on site by using an air separation unit. During the conventional process, the complete oxidation side reaction yield is approximately 5.6%, which contributes to direct $CO_2$ emissions from the process. The gaseous product stream from the main reactor is cooled and sent to a scrubber where water is used as the scrubbing media. EtO dissolves in water and leaves with the aqueous stream. The aqueous stream is sent to a distillation column where the EtO is recovered from the aqueous stream and is sent for downstream processing or product storage.

The main utility requirements for the conventional process are electricity and natural gas for heating. Other factors such as transportation and delivery costs would be similar for the conventional process and the process disclosed herein.

A cradle-to-gate GHG impact factor for CO produced through the processing of syngas was considered in this analysis. Although the GHG impact of syngas may be minimized with the use of biomass, steam methane reforming of natural gas may be used in some venues. This impact would be the total GHG emissions that are avoided by producing CO by using the process disclosed herein instead of through conventional processes and hence, considered as a GHG benefit.

GHG Assumptions

The block diagram for the process disclosed herein is shown in FIG. 12. In this process, $CO_2$, is assumed to be sourced from a sequestration pipeline. Ethanol is assumed to be available from a distribution system or refinery.

A process model to simulate the full-scale process for a plant producing 250 kt/year of EtO was developed. Electricity consumption, $CO_2$ requirement, and thermal energy input to the system were estimated using the process model. These estimates were used in the GHG LCA to estimate the total amount of $CO_2$ emitted per ton of EtO produced. Renewable and waste sources of energy were not considered for these utilities but could offer additional GHG benefits. To make comparisons easier, the GHG emissions for the C3-PEO and conventional processes are quantified in terms of the amount of $CO_{2-e}$ emitted per ton of EtO.

The outlet gas stream contains a mixture of products (CO, EtO, and $H_2O$), as well as the unreacted $CO_2$ and Et. This stream is used for partial reheating of the feed gases and is sent to a scrubbing section that uses $H_2O$ as the scrubbing agent. Product EtO is recovered in the water stream exiting this section, and the $H_2O$ and EtO mixture is distilled to recover EtO as the product similar to conventional EtO production. The gas stream leaving the scrubbing section with CO, $CO_2$, and unconverted Et is sent to a $CO_2$ capture system, where $CO_2$ is captured and recycled to the co-feed reactor. The outlet gas stream is a mixture of CO and Et and is sent to a cryogenic separation unit to condense Et from the mixture and obtain a pure product stream of CO. There are no commercial units for a CO and Et separation, but it should be similar to separating methane and CO. Unconverted Et is recycled to the co-feed reactor.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A method of catalyzing the abstraction of oxygen from carbon dioxide ($CO_2$) to form carbon monoxide (CO) comprising contacting a mixed molybdenum oxide catalyst, which comprises a silver oxide, a ruthenium oxide, or a mixture thereof,
   wherein the molar ratio of the silver oxide or the ruthenium oxide to molybdenum oxide is in the range of 1.0 to 0.5 to 1.0 to 5.0,
   with an appropriate $CO_2$ feed stream under suitable temperature and pressure conditions so as to abstract oxygen from the $CO_2$ to form CO.

2. The method of claim 1 wherein the mixed molybdenum oxide catalyst, further comprises a Group IA or Group IIA element promoter.

3. The method of claim 1 wherein the mixed molybdenum oxide catalyst, further comprises a support.

4. The method of claim 3 wherein the mixed molybdenum oxide catalyst, wherein the support is $Al_2O_3$, $SiO_2$, $TiO_2$, $ZrO_2$, $A_1PO_4$, carbon, graphite, or a mixture thereof.

5. The method of claim 1 wherein the mixed molybdenum oxide catalyst, wherein the mixed catalyst is a mixed silver/molybdenum oxide catalyst.

6. The method of claim 5 wherein the mixed silver/molybdenum oxide catalyst, wherein the molar ratio of $Ag_2O$ to $MoO_3$ is in the range of 1.0 to 0.5 to 1.0 to 5.0.

7. The method of claim 6 wherein the mixed silver/molybdenum oxide catalyst, wherein the molar ratio of $Ag_2O$ to $MoO_3$ is in the range of 1.0 to 0.5 to 1.0 to 4.0.

8. The method of claim 7 wherein the mixed silver/molybdenum oxide catalyst, wherein the molar ratio of $Ag_2O$ to $MoO_3$ is in the range of 1.0 to 0.5 to 1.0 to 2.0.

9. The method of claim 8 wherein the mixed silver/molybdenum oxide catalyst, wherein the molar ratio of $Ag_2O$ to $MoO_3$ is in the range of 1.0 to 1.0 to 1.0 to 3.0.

10. The method of claim 1 wherein the mixed molybdenum oxide catalyst, wherein the mixed catalyst is a mixed ruthenium/molybdenum oxide catalyst.

11. The method of claim 10 wherein the mixed ruthenium/molybdenum oxide catalyst, wherein the molar ratio of $RuO_2$ to $MoO_3$ is in the range of 1.0 to 0.5 to 1.0 to 5.0.

12. The method of claim 11 wherein the mixed ruthenium/molybdenum oxide catalyst, wherein the molar ratio of $RuO_2$ to $MoO_3$ is in the range of 1.0 to 0.5 to 1.0 to 4.0.

13. The method of claim 11 wherein the mixed ruthenium/molybdenum oxide catalyst, wherein the molar ratio of $RuO_2$ to $MoO_3$ is in the range of 1.0 to 0.5 to 1.0 to 2.0.

14. The method of claim 13 wherein the mixed ruthenium/molybdenum oxide catalyst, wherein the molar ratio of $RuO_2$ to $MoO_3$ is in the range of 1.0 to 0.5 to 1.0 to 3.0.

15. The method of claim 1 wherein the mixed molybdenum oxide catalyst, wherein the mixed catalyst is a mixed silver/ruthenium/molybdenum oxide catalyst.

16. The method of claim 15 wherein the mixed silver/ruthenium/molybdenum oxide catalyst wherein the molar ratio of $Ag_2O$ to $MoO_3$ is in the range of 1.0 to 0.5 to 1.0 to 5.0 and the molar ratio of $RuO_2$ to $MoO_3$ is in the range of 1.0 to 0.5 to 1.0 to 5.0.

17. The method of claim 16 wherein the mixed silver/ruthenium/molybdenum oxide catalyst wherein the molar ratio of $Ag_2O$ to $MoO_3$ is in the range of 1.0 to 1.0 to 1.0 to 4.0 and the molar ratio of $RuO_2$ to $MoO_3$ is in the range of 1.0 to 1.0 to 1.0 to 4.0.

18. The method of claim 1, wherein the mixed molybdenum oxide catalyst, and the appropriate $CO_2$ feed stream are reacted together at the same time.

19. The method of claim 1, wherein the mixed molybdenum oxide catalyst, and the appropriate $CO_2$ feed stream are reacted sequentially.

20. The method of claim 1, wherein the mixed molybdenum oxide catalyst, and the appropriate $CO_2$ feed stream are reacted sequentially in a chemical looping process.

21. The method of claim 1, wherein the mixed molybdenum oxide catalyst, and the appropriate $CO_2$ feed stream are reacted together in a fluidized bed.

* * * * *